US010592960B2

(12) United States Patent
Chu et al.

(10) Patent No.: US 10,592,960 B2
(45) Date of Patent: Mar. 17, 2020

(54) DETERMINING THERMAL INSULATION LEVELS OF CLOTHING TO WEAR AT A DESTINATION

(71) Applicant: Futurewei Technologies, Inc., Plano, TX (US)

(72) Inventors: Yaya Chu, San Jose, CA (US); I-Hsuan Yang, Santa Clara, CA (US)

(73) Assignee: FUTUREWEI TECHNOLOGIES, INC., Plano, TX (US)

( * ) Notice: Subject to any disclaimer, the term of this patent is extended or adjusted under 35 U.S.C. 154(b) by 84 days.

(21) Appl. No.: 15/847,747

(22) Filed: Dec. 19, 2017

(65) Prior Publication Data
US 2019/0188773 A1 Jun. 20, 2019

(51) Int. Cl.
*G06T 7/00* (2017.01)
*G01N 25/18* (2006.01)
(Continued)

(52) U.S. Cl.
CPC ......... *G06Q 30/0631* (2013.01); *G01N 25/18* (2013.01); *G06F 16/5866* (2019.01);
(Continued)

(58) Field of Classification Search
CPC ............ G06F 16/5866; G06Q 30/0631; G01N 25/18; G06K 9/00778; G06T 7/0004; G06T 2207/30124
See application file for complete search history.

(56) References Cited

U.S. PATENT DOCUMENTS 8,861,866 B2 * 10/2014 Zhang ................ G06K 9/00664
382/111
10,282,772 B2 * 5/2019 Giampaolo ........ G06Q 30/0631
(Continued)

FOREIGN PATENT DOCUMENTS

CN 102842102 A 12/2012
CN 106651310 A 5/2017
(Continued)

OTHER PUBLICATIONS

International Search Report dated Feb. 19, 2019, in PCT Application No. PCT/CN2018/116625, 10 pages.
(Continued)

*Primary Examiner* — Santiago Garcia
(74) *Attorney, Agent, or Firm* — Vierra Magen Marcus LLP

(57) ABSTRACT

The disclosure relates to determining thermal insulation levels of clothing a user should wear when traveling to a destination. To do this, a thermal insulation level of clothing worn by a user and levels worn by a crowd can be analyzed from images including the user or the crowd. A thermal sensitivity bias for the user can be determined by comparing those levels for similar locations. Environment data can then be collected for the destination. A thermal insulation level of clothing worn by the crowd for the destination can be predicted based on the environment data. This level can be adjusted with the bias for the user to generate a thermal insulation level of clothing to be worn by the user at the destination. An image having clothing with that level can be displayed to recommend a style of clothing for the user to wear at the destination.

19 Claims, 8 Drawing Sheets

(51) Int. Cl.
  *G06Q 30/06* (2012.01)
  *G06K 9/00* (2006.01)
  *G06F 16/58* (2019.01)
  *G06Q 50/14* (2012.01)

(52) U.S. Cl.
  CPC ........ *G06K 9/00778* (2013.01); *G06T 7/0004* (2013.01); *G06Q 50/14* (2013.01); *G06T 2207/30124* (2013.01)

(56) References Cited

U.S. PATENT DOCUMENTS

| | | | |
|---|---|---|---|
| 2013/0057544 A1* | 3/2013 | Oh | G06Q 30/06 345/419 |
| 2014/0180864 A1* | 6/2014 | Orlov | G06Q 30/0631 705/26.7 |
| 2014/0379426 A1* | 12/2014 | Guo | G06T 11/60 705/7.31 |
| 2015/0052004 A1* | 2/2015 | Jones | G06Q 30/0631 705/26.7 |
| 2015/0145671 A1* | 5/2015 | Cohen | G08B 21/18 340/539.11 |
| 2015/0302505 A1* | 10/2015 | Di | G06K 9/00362 705/26.7 |
| 2016/0055236 A1* | 2/2016 | Frank | G06Q 30/02 707/748 |
| 2016/0092956 A1* | 3/2016 | Su | G06Q 30/0643 705/26.5 |
| 2016/0189273 A1* | 6/2016 | Eramian | G06Q 30/0631 705/26.7 |
| 2016/0321547 A1* | 11/2016 | Johnson | G06Q 10/087 |
| 2017/0000277 A1* | 1/2017 | Johnson | G06Q 10/08 |
| 2017/0163938 A1* | 6/2017 | Yajima | G08B 21/02 |
| 2017/0345279 A1* | 11/2017 | Abraham | G08B 21/182 |
| 2017/0367917 A1* | 12/2017 | Donat | A41D 31/065 |
| 2018/0060937 A1* | 3/2018 | Shu | D06F 33/02 |
| 2018/0120873 A1* | 5/2018 | Radermacher | F24F 5/0017 |

FOREIGN PATENT DOCUMENTS

| | | |
|---|---|---|
| CN | 106767877 A | 5/2017 |
| CN | 106919605 A | 7/2017 |
| CN | 106973151 A | 7/2017 |
| CN | 107145520 A | 9/2017 |
| JP | 2003345872 A | 12/2003 |
| WO | 2017128008 A1 | 8/2017 |

OTHER PUBLICATIONS

ClosetSpace: combining curated outfit suggestions with the items in your own closet, allowing you to put together a stylish sartorial system at no extra cost (mobile APP); https://closetspace.com/women/shop.

Zhang et al.; Trip Outfits Advisor: Location-Oriented Clothing Recommendation (IEEE Transactions on Multimedia (vol. PP, Issue: 99) Apr. 24, 2017).

* cited by examiner

DETERMINING THERMAL INSULATION LEVELS OF CLOTHING TO WEAR AT A DESTINATION

FIELD

The disclosed technology relates to recommending thermal insulation levels of clothing for a user or identified individual when traveling to a destination.

BACKGROUND

Many geographic regions around the world experience large daily temperature changes many times a year. For example, daily temperatures in cities such as Shanghai, China during the spring and fall may exhibit large temperature swings from one day to the next. When living in or traveling to these geographic regions, especially during times of the year when large daily temperature swings may occur, determining what type of clothing to wear on a daily basis may be an important question to answer for a person to be comfortable.

Thanks to modern transportation systems, people are traveling to various destinations around the world more frequently. When traveling, a person may seek advice as to what type of clothing to wear at the destination. Such knowledge can avoid the problem of not having the proper clothing to wear to ensure that the person is comfortable during their time at the destination. Knowing what type of clothing to wear for the destination may be especially important when someone travels to a destination in which the temperature or weather varies significantly from where the person lives. Accordingly, it would be helpful to have a more accurate, efficient and intuitive way to determine the type of clothing that is appropriate when traveling to a destination and/or when living in geographical locations in which the temperatures vary on a daily basis.

BRIEF SUMMARY

According to one aspect of the present disclosure, there is provided a method that includes determining thermal insulation levels for clothing at a computer or mobile device, comprising: analyzing a thermal insulation level of clothing worn by a user in one or more images including the user; analyzing a thermal insulation level of clothing worn by the crowd of individuals in the one or more images; determining a thermal sensitivity bias for the user by comparison of the thermal insulation level of clothing worn by the user to the thermal insulation level of clothing worn by the crowd; collecting environment data based on at least one of time and location of a destination from a database; predicting a thermal insulation level of clothing worn by the crowd for the destination based on the destination and the collected environment data; generating a thermal insulation level of clothing worn by the user at the destination comprised of the thermal insulation level of the clothing worn by the crowd for the destination adjusted by the thermal sensitivity bias for the user; identifying an image from the database having clothing with a thermal insulation level comparable to the thermal insulation level of clothing worn by the user at the destination; and recommending a style of clothing to the user using a computer or mobile device based on the identified image.

Optionally, in any of the preceding aspects, another implementation of the aspect provides that the method further includes collecting past environment, time and location data from one or more images including the user and/or a crowd of individuals; and correlating the past environment, time and location data to a thermal insulation level of clothing worn by the user or crowd of individuals in the same image.

Optionally, in any of the preceding aspects, another implementation of the aspect provides that the method further includes wherein the one or more images include the user in each of a plurality of the one or more images; the one or more images include the crowd of individuals in each of a plurality of the one or more images; or the one or more images include the user and the crowd of individuals at a same location and at the same time of year in each of a plurality of the one or more images.

Optionally, in any of the preceding aspects, another implementation of the aspect provides that the method further includes wherein determining the thermal sensitivity bias for the user includes averaging multiple comparisons of thermal insulation levels of clothing worn by the user to thermal insulation levels of clothing worn by the crowd at a same time, location, and environment.

Optionally, in any of the preceding aspects, another implementation of the aspect provides that the method further includes wherein: analyzing the thermal insulation level of clothing worn by the crowd includes inputting the one or more images including the crowd into a trained second model, analyzing the thermal insulation level of clothing worn by the user includes inputting the one or more images including the user into a trained first model, and predicting the thermal insulation level of clothing worn by the crowd at the destination includes inputting the destination and collected environment data into the trained second model.

Optionally, in any of the preceding aspects, another implementation of the aspect provides that the method further includes wherein identifying an image from the database comprises one of: matching the thermal insulation level of clothing worn by the user at the destination with a thermal insulation level of clothing worn by the user in the one or more images including the user; matching the thermal insulation level of clothing worn by the user at the destination with a thermal insulation level of clothing worn by the crowd in the one or more images including the crowd; or matching the thermal insulation level of clothing worn by the user at the destination with a thermal insulation level of clothing in an image from a vendor.

Optionally, in any of the preceding aspects, another implementation of the aspect provides that the method further includes displaying the image from the vendor to the user, wherein the image from the vendor has a link to a website of the vendor, the website being capable of selling the clothing in the image from the vendor to the user.

Optionally, in any of the preceding aspects, another implementation of the aspect provides that the method further includes wherein recommending a style of clothing to the user includes one of displaying the matched clothing worn by the user in the one or more images including the user, or displaying the matched clothing in the image from a vendor when the clothing in the image from a vendor was previously viewed at a website of the vendor.

Optionally, in any of the preceding aspects, another implementation of the aspect provides that the method further includes wherein the database comprises average thermal insulation levels of clothing worn by the crowd in a plurality of locations, times of year and environments.

Optionally, in any of the preceding aspects, another implementation of the aspect provides that the method further includes wherein: the destination includes one of a trip itinerary, or a trip time and location; the collected environment data includes weather information for the destination; and the destination is at a different location than a location of the user's primary residence.

According to one aspect of the present disclosure, there is provided a determining thermal insulation levels for clothing device, comprising: a memory storage comprising instructions; and one or more processors in communication with the memory storage, wherein the one or more processors execute the instructions to: determine a thermal sensitivity bias for a user by comparison of the thermal insulation level of clothing worn by the user in one or more images including the user and a crowd of individuals to the thermal insulation level of clothing worn by the crowd in the one or more images; collect environment data based on at least one of time and location of a destination from a database; predict a thermal insulation level of clothing worn by the crowd for the destination based on the destination and the collected environment data; generate a thermal insulation level of clothing worn by the user at the destination comprised of the thermal insulation level of the clothing worn by the crowd for the destination adjusted by the thermal sensitivity bias for the user; and identify an image from the database having clothing with a thermal insulation level comparable to the thermal insulation level of clothing worn by the user at the destination.

According to one aspect of the present disclosure, there is provided a non-transitory computer-readable medium storing computer instructions for determining thermal insulation levels for clothing at a computer or mobile device, that when the computer instructions are executed by one or more processors, cause the one or more processors to perform the steps of: determining a thermal sensitivity bias for a user by comparison of the thermal insulation level of clothing worn by the user in one or more images including the user and a crowd of individuals to the thermal insulation level of clothing worn by the crowd in the one or more images; collecting environment data based on at least one of time and location of a destination from a database; predicting a thermal insulation level of clothing worn by the crowd for the destination based on the destination and the collected environment data; generating a thermal insulation level of clothing worn by the user at the destination comprised of the thermal insulation level of the clothing worn by the crowd for the destination adjusted by the thermal sensitivity bias for the user; and identifying an image from the database having clothing with a thermal insulation level comparable to the thermal insulation level of clothing worn by the user at the destination.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

Aspects of the present disclosure are illustrated by way of example and are not limited by the accompanying figures for which like references indicate like elements.

DETAILED DESCRIPTION

Figure 1A:
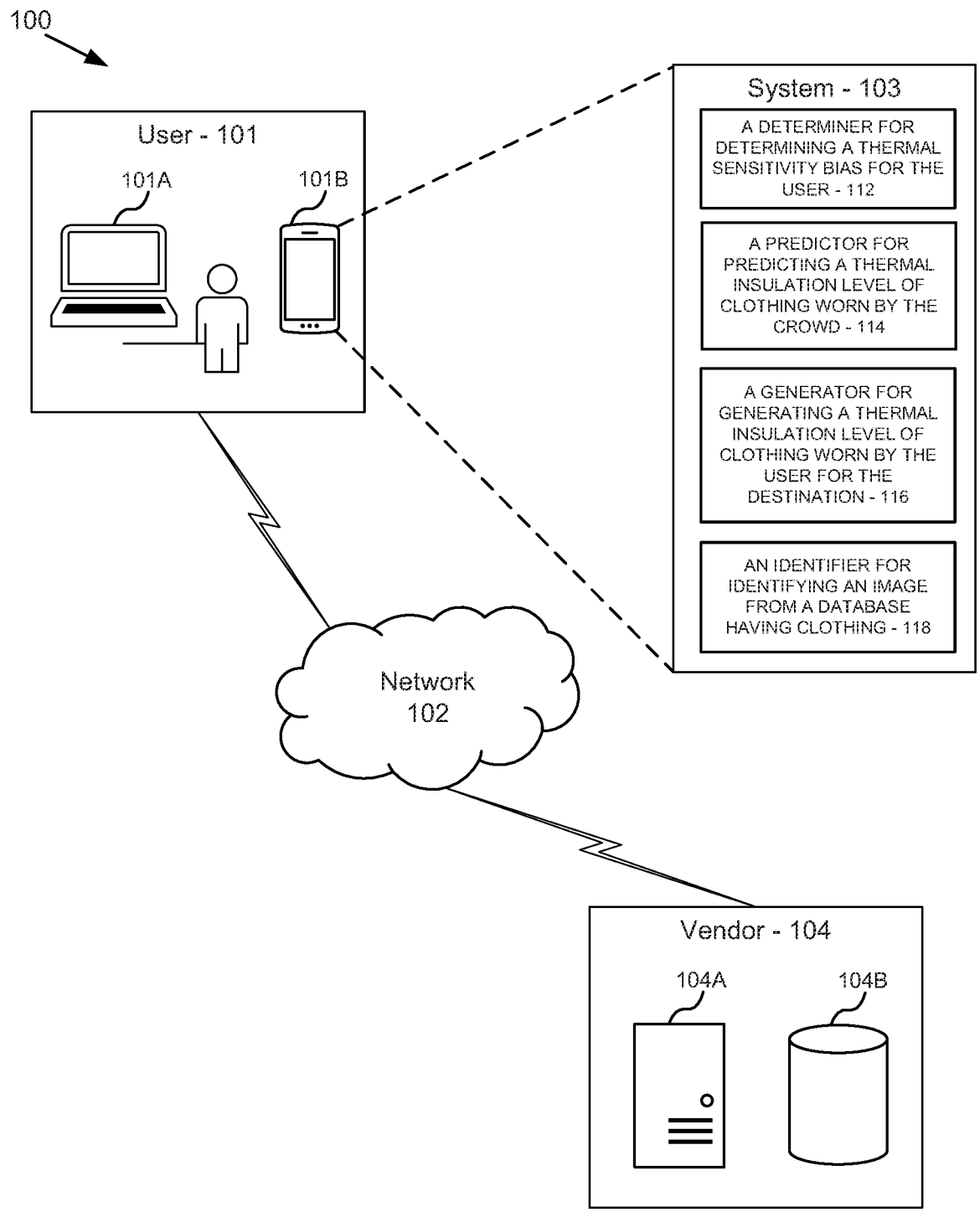
FIG. 1A illustrates a network environment that can be used to implement various embodiments.

The disclosed technology relates to a user or cloud based device to recommend thermal insulation (e.g., warmness) levels of clothing. Embodiments described herein can recommend thermal insulation levels of clothes (including but not limited to thickness, material, layers, style) by determining a thermal sensitivity bias for thermal insulation levels of clothes worn by a user as compared to other users. The thermal sensitivity bias can be based, for example, on differences in the thermal insulation level of clothes worn by the user compared to the average level of clothes worn by individuals in a crowd. For example, the sensitivity bias may be determined based on images of clothing worn by the user (some may include user with a crowd of individuals) and images of clothing worn by individuals in the crowd at the same or similar geographic regions, during same or similar time periods, or during the same or similar temperature conditions.

In one embodiment, a first model is trained with personal thermal insulation levels of clothing worn by the user taken from images or photos of the user, for example, at different locations and dates. The photos may be mined from the user's computer, phone and/or database of images residing on one or more servers in the cloud. Similarly, a second model is trained with thermal insulation levels of clothing worn by individuals of a crowd taken from images or photos of crowds, for example, at different locations and dates. Personal thermal insulation levels of the user are compared to thermal insulation levels of clothes worn by the crowd to determine a thermal sensitivity bias for a user. For instance, in one example embodiment, differences of the compared levels at a number of same locations/dates can be averaged to give a number that represents an amount (i.e., the sensitivity bias for the user) the user is usually dressed warmer or colder than the crowd.

When the user prepares to travel to a destination (or if the user lives in a geographical region in which temperature swings are common), environment data, such as predicted weather, can be collected at the destination or retrieved from historical environment data previously collected. Applying the collected environment data and the destination location to the second model, the thermal insulation level of clothing worn by the crowd at the destination (e.g., and for the environment data) may be predicted. The thermal insulation level for clothing to be worn by the user at predicted destination may then be generated using the predicted thermal insulation level of clothing worn by the crowd at destination adjusted by the thermal sensitivity bias of the user. Based on the generated thermal insulation level for clothing to be worn by the user at predicted destination, an image(s) may be identified from a database in which the image(s) have clothing with a thermal insulation level comparable to the generated thermal insulation level for clothing to be worn by the user at predicted destination. In one embodiment, the image(s) of clothing can be from the user's photos, crowd photos or a vendor who sells clothing. A style of clothing can then be recommended to the user based on the identified image(s).

According to embodiments, use of the term "user" herein, such as in descriptions of determining thermal insulation levels for clothing to be worn by a user or recommending thermal insulation levels of clothing for a user (e.g., when traveling to a destination) may apply to an identified individual. For example, a "user" maybe the owner of a mobile device, computer (e.g., device 101B) or cloud based service that provides the determination or recommendation. In other cases, the "user" may also be another person such as a child, parent or other relative of the owner. It is also considered that the "user" may be any other individual person for whom images that include that individual are accessible to or in (e.g., at 122 of FIG. 1B; or block 210 of FIG. 2) the mobile device, computer or cloud based service that provides the determination or recommendation. In one embodiment, the "user" is an individual other than the person operating user device 101B or system 103.

It is understood that the present embodiments of the invention may be implemented in many different forms and that claims scopes should not be construed as being limited to the embodiments set forth herein. Rather, these embodiments are provided so that this disclosure will be thorough and complete and will fully convey the inventive embodiment concepts to those skilled in the art. Indeed, the invention is intended to cover alternatives, modifications and equivalents of these embodiments, which are included within the scope and spirit of the invention as defined by the appended claims. Furthermore, in the following detailed description of the present embodiments of the invention, numerous specific details are set forth in order to provide a thorough understanding. However, it will be clear to those of ordinary skill in the art that the present embodiments of the invention may be practiced without such specific details.

FIG. 1A illustrates a network environment 100 that can be used to implement various embodiments. Network environment 100 is shown having user 101, network 102, system 103 and vendor 104. User 101 has user devices 101A and 101B. System 103 is shown as part of user device 101B. Network environment 100 can provide content through network 102 as requested by user device 101A, user device 101B, system 103, vendor 104, and other users of the network.

Network environment 100 may include one or more users, such as user 101, having user devices, such as user devices 101A or 101B, for determining thermal insulation levels of clothing to wear at a destination. User 101 is shown having access to or using user device 101A shown as a computer, and user device 101B shown as a mobile phone. User device 101A or 101B may be for example and without limitation, desktop computers, hand-held devices, laptops or other portable computers, network computers, mobile phones, and the like. Examples of user device 101A or 101B may include a mobile wireless communication device, wireless transmit/receive unit (WTRU), mobile station, fixed or mobile subscriber unit, pager, cellular telephone, personal digital assistant (PDA), smartphone, smartwatch, laptop, computer, touchpad, tablet computer, or consumer electronics device.

Network 102 is a data network connecting system 103 to vendor 104 (e.g., to server 104A) through one or more of user devices 101A and 101B. Network 102 may be or include a local area network, intranet, the Internet, an information centric network (ICN), a computer network, a cellular network and/or another network. Network 102 may include other components not shown, such as network controllers, managers, base stations, routers and the like.

User device 101B includes system 103 for determining thermal insulation levels of clothing to wear at a destination. It can be appreciated the system 103 may exist on device 101A as well on user device 101B, or any other user device. In some embodiments, system 103 may determine thermal insulation levels of clothing to wear at a destination or geographic region. At 112, system 103 may include determiner 112 that determines a thermal sensitivity bias for the user 101. Determining the thermal sensitivity bias may include: (1) analyzing a thermal insulation level of clothing worn by a user in one or more images including a user and a crowd of individuals; (2) analyzing a thermal insulation level of clothing worn by the crowd in the one or more images; and then (3) determining the thermal sensitivity bias for the user by comparison of the thermal insulation level of clothing worn by the user at to the thermal insulation level of clothing worn by the crowd.

At 114, the system 103 may comprise predictor 114 that predicts a thermal insulation level of clothing worn by the crowd for the destination. Here, predicting the thermal insulation level may include (1) collecting environment data based on at least one of time and location of a destination from a database; and then (2) predicting a thermal insulation level of clothing worn by the crowd for the destination based on the destination and collected environment data.

At 116, the system 103 may include generator 116 that generates a thermal insulation level of clothing worn by the user for the destination. Here, generating may include generating a thermal insulation level of clothing worn by the user for the destination comprised of the thermal insulation level of the clothing worn by the crowd for the destination (e.g., as predicted by predictor 114) adjusted by the thermal sensitivity bias for the user (e.g., as determined by determiner 112 above).

At 118, the system 103 may have identifier 118 that may identify an image from a database having clothing. Here, identifying may include identifying an image from the database having clothing with a thermal insulation level comparable to the thermal insulation level of clothing worn by the user for the destination (e.g., as generated by generator 116 above). Here, identifying may also include recommending a style of clothing to the user using a computer or mobile device based on the identified image (e.g., as identified by identifier 118).

In some cases, system 103 may be part of an operating system, a mobile phone application, a client/server application or another component of user device 101B. In some cases, system 103 may be or have a memory storage comprising instructions to be executed by one or more processors in communication with the memory storage, for determining thermal insulation levels of clothing to wear at a destination. In some cases, system 103 may be or have a non-transitory computer-readable medium storing computer instructions for determining thermal insulation levels of clothing to wear at a destination.

In other instances (not shown), user device 101B may have access to system 103 which is not part of that device but is a cloud based device, system or service that is capable of determining thermal insulation levels of clothing to wear at a destination, and communicating the level (e.g., see 132 of FIG. 1B explained below), images having that level (e.g., see 134 of FIG. 1B) or a style of clothing (e.g., see 136 of FIG. 1B explained below) to user 101 through user device 101A. As a cloud based device, system 103 may be accessible from a cloud based server, website or other application hosting system 103 to user device 101B through network 102.

The functional components of system 103 (e.g., determiner 112, predictor 114, generator 116 and identifier 118) may be referred to as processors, modules or components, and may each be executed on a single processor or separate processors. In some embodiments, they could be implemented with any combination of hardware and/or software. They may further include one or more elements for performing any one or combination of processes described in the embodiments.

Network environment 100 may further include vendor 104 having server 104A and vendor database 104B. Database 104B may be one or more databases that store images of clothes sold by vendor 104, such as advertising images, catalog images or other images as known in the clothing or textile sales industry; and that is accessible by server 104A. Server 104A may include or implement a vendor website such as a website for sales and/or marketing of the clothing in database 104B through network 102 to user 101 through user devices 101A and 101B. As will be noted further, server 104A and/or database 104B may be able to recognize and determine relationships between the clothing in images stored in database 104B and the thermal insulation level of the clothing in the images. Thus, when a thermal insulation level of clothing is input into or searched for in database 104B, it can output clothing in an image from vendor 104, such as an image stored in the database that has the thermal insulation level that was input. The images in database 104B may be part of data content, such as files, video images, photographs, computer graphics and the like.

Figure 6:
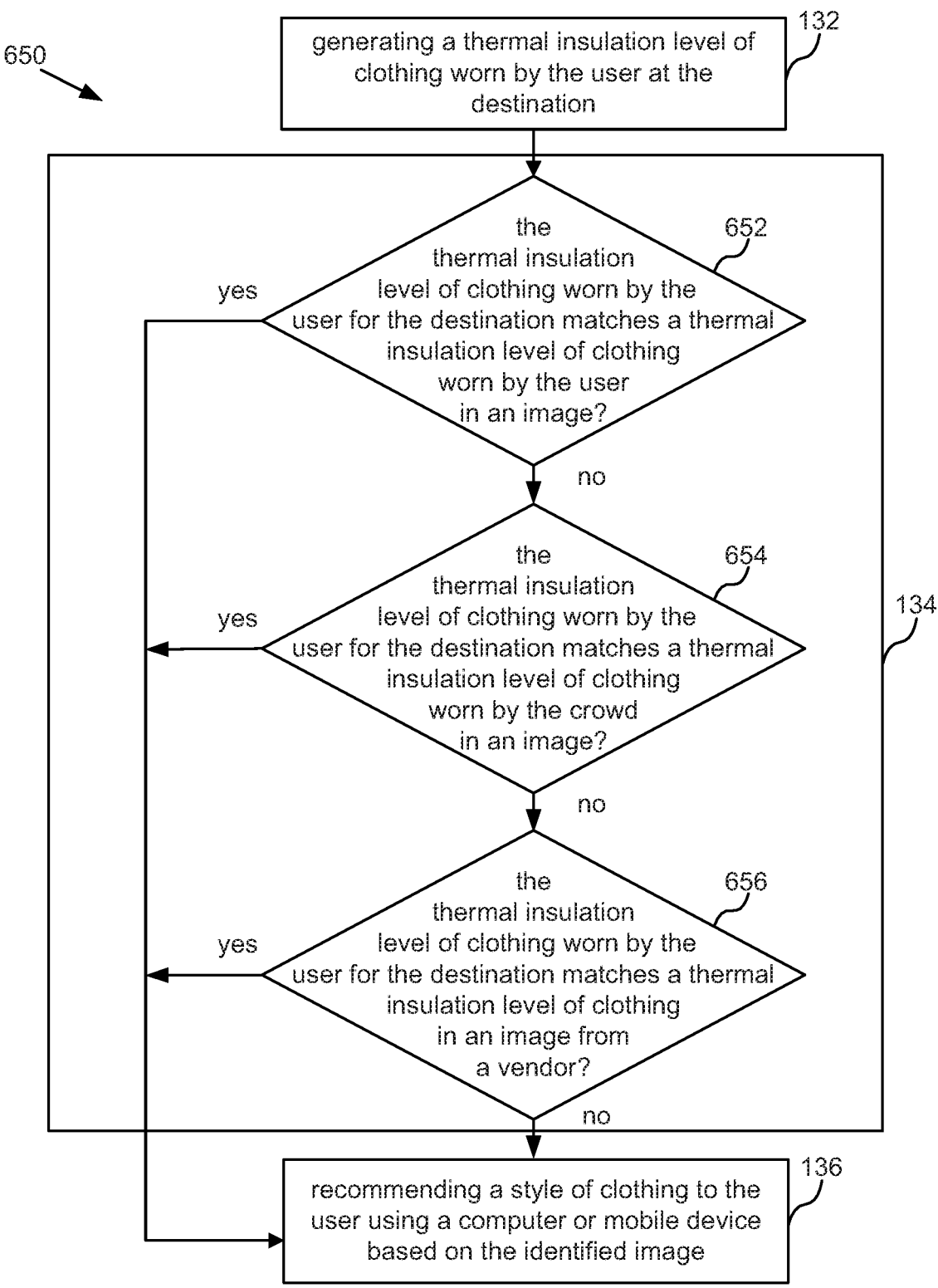
FIG. 6 is a flow diagram of a process for identifying an image according to example embodiments.

Accordingly, the network 102 may communicate with server 104A to provide (e.g., be a "producer" of) images of clothing matching the thermal insulation level of clothing worn by the user for the destination as noted herein (e.g., see 656 of FIG. 6). In some instances, server 104A may be one or more computer servers capable of searching for providing these images from database 104B as requested by user device 101B or system 103, such as through a website or other application hosted on server 104A.

As noted above, a thermal insulation level of clothes may be recommended to a user. It is appreciated, however, that the embodiments are not limited to a single destination or single date but are able to recommend the level for any of various dates at one location, any of various locations on a single date, or any combination thereof. The embodiments described may also recommend the level for any of various times of day/night for any of the combination of various locations and/or dates. In addition, the embodiments may recommend the thermal insulation level for any of various environment data (e.g., weather) for any of the combination of various locations, dates and times (optionally).

Figure 1B:
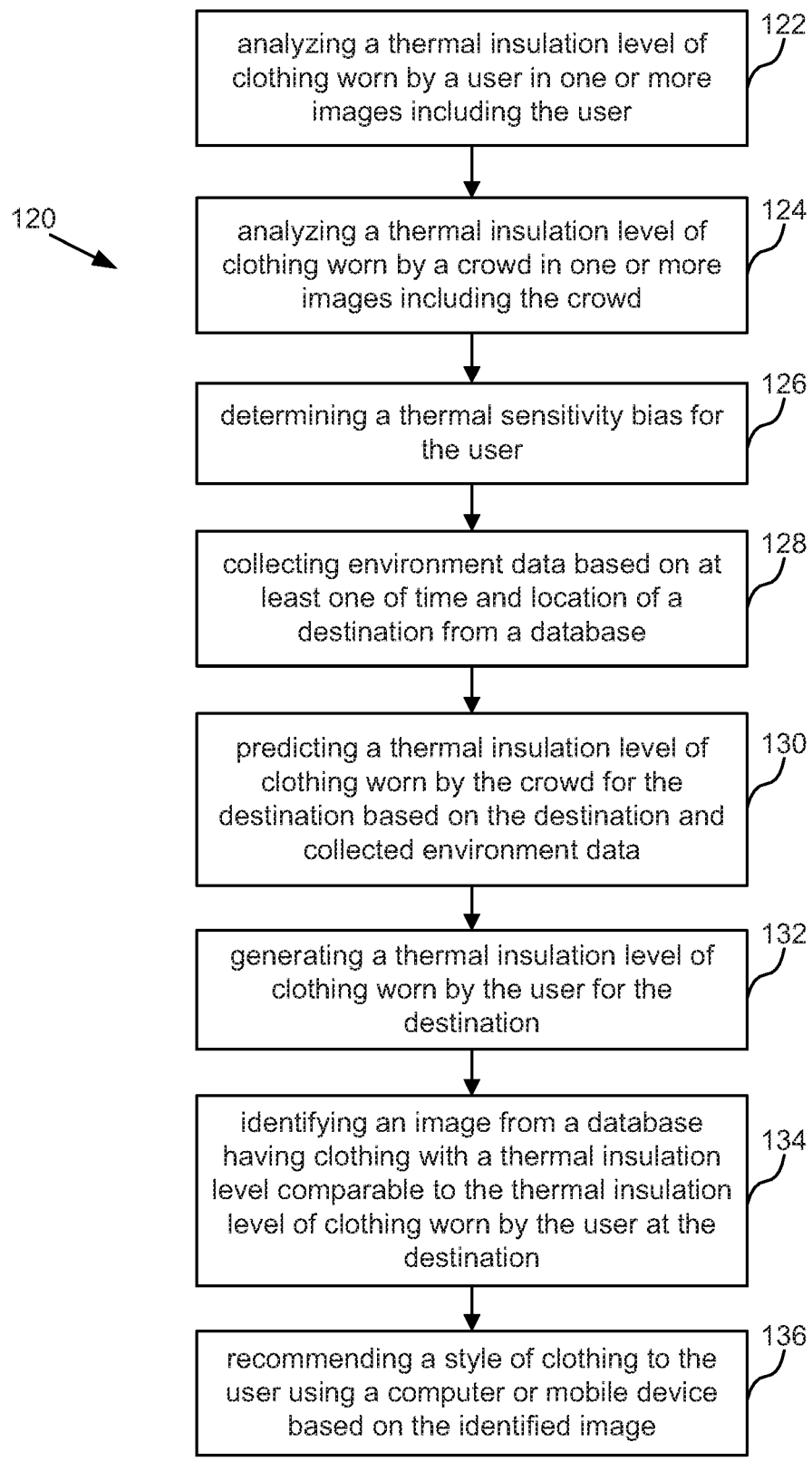
FIG. 1B is a flow diagram of a process for determining thermal insulation levels of clothing to wear at a destination, according to example embodiments.

FIG. 1B is a flow diagram of a process 120 for determining thermal insulation levels of clothing to wear at a destination, according to example embodiments. Process 120 may be performed at or by user device 101B or system 103 for purposes of discussion. However, it is appreciated that any component illustrated in FIGS. 1A, 2-5, and 7 may be employed to implement the process.

Process 120 begins at 122 where a thermal insulation level of clothing worn by a user in one or more images including the user is analyzed. Analyzing the thermal insulation level of clothing worn by the user at 122 may include using a first model that was trained by inputting the one or more images including the user into the first model.

According to embodiments, the one or more images may be part of data content, such as files, video images, photographs, computer graphics and the like. In some cases, the images may be "live" images such as from a camera of a device in real-time and are not limited to previously taken photos or images stored in a database or memory. This may include various resolutions, data size, 2-dimensional and 3-dimensional media images or frames, etc. For some embodiments, the images described herein may include the user in each of a number of images; a crowd of individuals in each of a number of images; or the user and the crowd of individuals at a same location and at the same time of year in each of the number of images.

For example, prior to 122, an untrained first model of user device 101B or system 103 may be trained by inputting images and identifying thermal insulation levels of clothing worn by the user at various configurations in the images of the user, such as at various locations on various dates. In some cases, the untrained first model may be trained to be the trained model at block 240, as explained below in detail with reference to FIG. 2.

At 122, after the first untrained model is trained, when an image including the user is input into trained model at block 240 of user device 101B or system 103 at 122, the model outputs the thermal insulation level of clothing worn by the user at that configuration, and what that configuration is (e.g., see blocks 410, 415, 430 and 432 of FIG. 4 described below).

This insulation level may be an average of insulation levels of clothes that the user wore in one or more images for a particular configuration. It can be appreciated that instead of an average, another mathematical combination such as using least squares or the like can be used to determine the output level, and that the insulation level is not limited to an average of levels. In some cases, the analyzing at 122 may include inputting a certain image of the user having a certain configuration into the first model, and then storing the output thermal insulation level of clothing worn by the user for that configuration and what that configuration is, such as for comparison at 126.

According to embodiments, a configuration may include a location or a destination. In some cases, a configuration may include or be data identifying a geographical location; time of year or one or more dates; and a time period or range of hours or the dates. The configuration may also include environment data such as a forecasted (or predicted) weather for the geographical location, such as forecast by a weather service, new channel, internet service, internet application or other forecast entity. For some embodiments, a configuration may include environment, time and location data. For example, a configuration may include data describing predicted weather for a destination location and date, as well as describing the destination location and date. In some cases, the configuration may be a combination of one or more of the above features and may be referred to herein as a full configuration.

According to some embodiments, uses of "configuration" or "full configuration" herein describe a "similar" configuration that includes a range of factors. For example, a "similar" configuration may be a first geographic region having a range of distance (e.g., area) or environment having a range of weather, as compared to a second geographic region or environment. In one example, a "similar" configuration that may include data identifying a "similar" geographical location; "similar" one or more dates; "similar" time period; and/or "similar" environment data. In some instances, data identifying a "similar" geographical location may identify a range of locations within a certain number of miles or kilometers (km) of a specific location, town or city. In one example, a similar location may be within a 50 km radius or 60 km radius from the Toronto. In some instances, data identifying a "similar" one or more dates may identify a range of dates within a certain number of days a specific date, such as of a travel itinerary. In one example, a similar one or more dates may be within 2 or 7 days from Jan. 24, 2018. In some instances, data identifying a "similar" time period may identify a range of hours or dates within a certain number of hours or days a specific time period, such as of a travel itinerary. In one example, a similar time period may be within 4 or 6 hours from 9 am to 5 pm pst. on Jul. 4, 2018. In some instances, data identifying "similar" environment data may identify a range of weather or temperature within a certain amount of percipitation, number of degrees F. or C in temperature of a specific weather forecast. In one example, similar environment data may be within a half inch of rain and 5 or 10 degrees F. of a weather forecast for one inch of rain over a day, a temperature high of 78 degrees, and a temperature low of 55 degrees for the day. In some embodiments, a "similar" configuration may include the "same" configuration, such as the original configuration, without the range(s).

At 124 a thermal insulation level of clothing worn by a crowd of individuals in one or more images including the crowd is analyzed. Analyzing the thermal insulation level of clothing worn by the crowd at 124 may include using a previously trained a "second" model that was trained by inputting the one or more images including the crowd into the second model.

In some embodiments, an untrained second model of user device 101B or system 103 may be trained by inputting images and identifying thermal insulation levels of clothing worn by individuals of a crowd at various configurations in the images of the crowd, such as at various locations on various dates. In some other embodiments, the untrained second model may be trained to be the trained model at block 340, as explained below in detail with reference to FIG. 3.

At 124, after the second model is trained, when a configuration is input into the trained model at block 340 of user device 101B or system 103, the model outputs the thermal insulation level of clothing worn by the crowd. In some embodiments, it may also output the type of configuration (e.g., see blocks 430, 435 and 436 of FIG. 4 described below). This thermal insulation level, as noted above, may be an average of insulation levels of clothes that individuals of one or more crowds wore in one or more images for that configuration.

In some embodiments, the analyzing at 124 may include inputting the same configuration or the same image into the second model as input into the first model at 122. The output of the thermal insulation level of clothing worn by the crowd for that configuration can be stored, such as for comparison at 126.

As previously discussed, it may be difficult for someone to determine what thermal insulation level of clothing to wear at a destination location on a date if they have not visited that location or have only visited that location during a different season of the year. For example, for someone who lives in San Jose, Calif., it can be difficult to determine what to wear during a trip to Quebec, Canada. For instance, in December, the difference in temperature and weather patterns between the two cities may vary significantly. In this case, a weather forecast may describe that it is 20 degrees C. in Quebec, or that there is a 15 degree C. temperature drop is forecast from one date to the next. However, the temperature and weather patterns alone may not sufficiently provide enough information to recommend a thermal insulation level of clothing for the user to wear during the trip to Quebec, as they fail to consider "personal" (user) thermal sensitivity biases and preferences of the user. For example, for someone who has never visited Quebec, even in light of that forecast, it may still be difficult to figure out whether the thermal insulation level of clothing they should pack should include a coat; a coat and sweater; boots and gloves; a thinner jacket or a thicker jacket because that person may have personal preferences or sensitivities to weather and temperature changes that are not simply accounted for by the forecast alone. The thermal sensitivity bias is designed to account for these preferences and sensitivities.

For some embodiments, it may be difficult for someone to determine what thermal insulation level of clothing to wear at a destination location on a date that they have previously experienced due to a substantial change in weather at that destination location on that date. For example, for someone who lives in San Jose, Calif., it can be difficult to determine what to wear on April 11 of this year even if that person has lived for for years because there is going to be a substantial change in weather, such as snow, thunder storms, or a heat wave on that date.

At 126, a thermal sensitivity bias for the user is determined, such as by comparison of the thermal insulation level of clothing worn by the user at 122 to the thermal insulation level of clothing worn by the crowd at 124. In one example, user device 101B or system 103 calculates the thermal sensitivity bias for the user by subtracting the thermal insulation level of clothing worn by the crowd at 124 from the thermal insulation level of clothing worn by the user at 122. It can be appreciated that other calculations may be considered, including using least squares, or subtracting the thermal insulation level at 124 from that at 122.

Determining a thermal sensitivity bias for the user at 126 may include comparing the stored output thermal insulation level of clothing worn by the user at 122 and the crowd at 124 for the same configuration or for the same image input at 122 and 124 (e.g., see blocks 432, 436 and 438 of FIG. 4), such as by subtracting the level of 124 form that of 122. In some embodiments, averaging multiple comparisons of the thermal insulation level of clothing worn by the user at 122 to the thermal insulation level of clothing worn by the crowd at 124.

In some other embodiments, at 126, determiner 112 determines a thermal sensitivity bias for the user 101, by comparing as noted above. In some embodiments, determining a thermal sensitivity bias for the user may be a thermal sensitivity bias for the user at block 438, as explained below in detail with reference to FIG. 4.

At 128, the environment data is collected based on at least one of time and location of a destination from a database. The collection of environment data at 128 may include user device 101B or system 103 receiving a configuration, such as a destination including at least a location and one or more dates during which the user be at that location. In some embodiments, the collection of environment data 128 includes receiving an input identifying a destination location and date(s). For some embodiments, the input identifies a configuration including the received destination. For example, the input may be a trip itinerary, a trip time and location, or a trip configuration. The trip itinerary, may be used by user device 101B or system 103 to calculate a trip time and location; and may be used to calculate a trip configuration by adding weather conditions or forecast information to the trip time and location.

In some embodiments, the input is a manual user input at user device 101B or system 103, or is user data existing on user device 101B or in system 103. Some examples include the user inputting data using a keyboard, mouse, touchscreen or microphone at the device or into the system. Other examples of input include the user device 101B or system 103 mining data from a calendar, scheduler or travel itinerary from the device, system or another device, such as a database, connected to the user device or system, such as through network 102.

In some embodiments, the environment data collected at 128 includes a weather forecast (or prediction) for the received configuration, such as the predicted temperature, humidity, precipitation and wind for the destination location and dates. The weather forecast may be collected by user device 101B or system 103 from a network, application on user device 101B, the Internet or another source of weather forecasts. In some cases, data collection includes inputting a time and location of a destination from a database into a network, or another source of environment data, which outputs the environment data of 128 (e.g., see blocks 510, 512 and 514 of FIG. 5 described below).

In some embodiments, the collected data at 128 is used to create a full configuration based on the geographic location, date(s) of year, times of day/night and predicted weather for the destination or received input or configuration. In one example, the full configuration provides a temperature range over the time period for the destination location.

At 130 a thermal insulation level of clothing worn by the crowd for the destination can be predicted based on the destination and collected environment data of 128. This may be or include predicting a thermal insulation level of clothing worn by the crowd for the configuration or the full configuration collected at 128. In some cases, 130 may include using a previously trained second model on user device 101B or system 103 as described for 124. For some embodiments, the second trained model is explained below in detail below with reference to FIG. 3.

For example, at 130, when the configuration or the full configuration collected at 128 is input into the trained second model at 130, the model outputs the thermal insulation level of clothing worn by the crowd for the specified configuration. In some cases, 130 includes or is inputting a time and location of a destination from a database, and optionally the collected environment data of 128 into the trained second model, which outputs a thermal insulation level of clothing worn by the crowd for the destination (e.g., see blocks 510, 514, 515 and 518 of FIG. 5 described below). In some case, 130 includes predictor 114 predicting a thermal insulation level of clothing worn by the crowd using the second trained model, as noted above.

At 132 a thermal insulation level of clothing worn by the user for the destination can be generated based on the thermal insulation level of the clothing worn by the crowd for the same destination predicted at 130 adjusted by the thermal sensitivity bias for the user determined at 126. In one example, user device 101B or system 103 generates the thermal insulation level of clothing worn by the user for the destination at 132 by adding the thermal sensitivity bias for the user determined at 126 to the thermal insulation level of the clothing worn by the crowd for the destination predicted at 130 (e.g., see blocks 516, 438 and 518 of FIG. 5 described below). It can be appreciated that other calculations for adjusting to the thermal insulation level of the clothing worn by the crowd may be considered, including use of least squares or adding a portion of the thermal insulation level determined at 126 to the thermal insulation level determined at 130.

In other embodiments, an image of data of the thermal insulation level of clothing worn by the user for the destination may not exist in the first model because there will not be an image of the user in that configuration or location. However, there may be an image of the user wearing the thermal insulation level of clothing generated at 132 in another image taken at a different configuration or location for which clothing worn by the user had a similar (or the same) thermal insulation level as that for the destination to which the user is traveling.

In another embodiment, generator 116 generates a thermal insulation level of clothing worn by the user for the destination, including the thermal insulation level of the clothing worn by the crowd for the destination and adjusted by the thermal sensitivity bias for the user, as noted above. In some cases, generating a thermal insulation level of clothing worn by the user for the destination may be a thermal insulation level of clothing, as explained below in detail with reference to FIG. 5.

At 134, an image from the database can be identified that is clothing with a thermal insulation level comparable to the thermal insulation level of clothing worn by the user for the destination from thermal insulation level generated at 132. Identifying an image at 134 may include user device 101B or system 103 receiving the thermal insulation level at 132 and looking up thermal insulation levels identified for clothing in a database to make the comparison. In some cases, identifying an image at 134 includes comparing the thermal insulation level generated at 132 to levels in the database to find a level that is equal to the level thermal insulation level generated at 132. At 134, process 120 may then identify the clothing the image in the database having the thermal insulation level that is equal with the thermal insulation level generated at 132. In other examples, making the comparison of the thermal insulation levels at 134 includes finding a thermal insulation level in the database within a certain threshold, such as 5 percent or 10 percent, of the thermal insulation level generated at 132.

In some other embodiments, at 134, the thermal insulation level generated at 132 is input into the first model and/or second model, and the first model and/or second model output a picture of the user and/or an individual of the crowd wearing the clothing having the level comparable to the thermal insulation level generated at 132 (e.g., see 652 and 654 of FIG. 6 described below).

In other embodiments, identifying an image at 134 includes accessing storage, such as a database, flash memory, etc., at a location remote from the user device 101B or system 103 via network 102. In some embodiments, the storage may be a clothing vendor's database, such as database 104B, and may be accessed through server 104A using network 102 (e.g., see 656 of FIG. 6 explained below).

In some embodiments, identifying an image at 134 includes identifier 118 identifying an image from the storage, as noted above. Other embodiments are explained below in detail with reference to FIG. 6.

At 136, a style of clothing is recommended to the user based on the identified image of 134. In some embodiments, the recommending at 136 includes user device 101B or system 103 receiving the image generated at 134 from the first model and recommending the clothing in the received image to the user by displaying that identified image. In this case, because that image includes clothing worn by the user, the clothing in that image may be described as having the user's "style" (e.g., see 652 of FIG. 6 explained above).

In another embodiment, the recommending at 136 includes user device 101B or system 103 receiving one or more images identified at 134 from a vendor database 104B having the thermal insulation level generated at 132, and recommending a style of clothing to the user based on one of the received images of clothing. For example, the recommendation may be based on vendor 104 having information indicating that the user was previously interested in that clothing/image, such as based on a cookie or web click information stored at server 104A or database 104B. In this case, due to the information, the clothing in that image may be described as having the user's "style" (e.g., see 656 of FIG. 6 explained above).

In one embodiment, the thermal sensitivity bias for the user is not determined or used to adjust the thermal insulation level predicted at 130.

Figure 2:
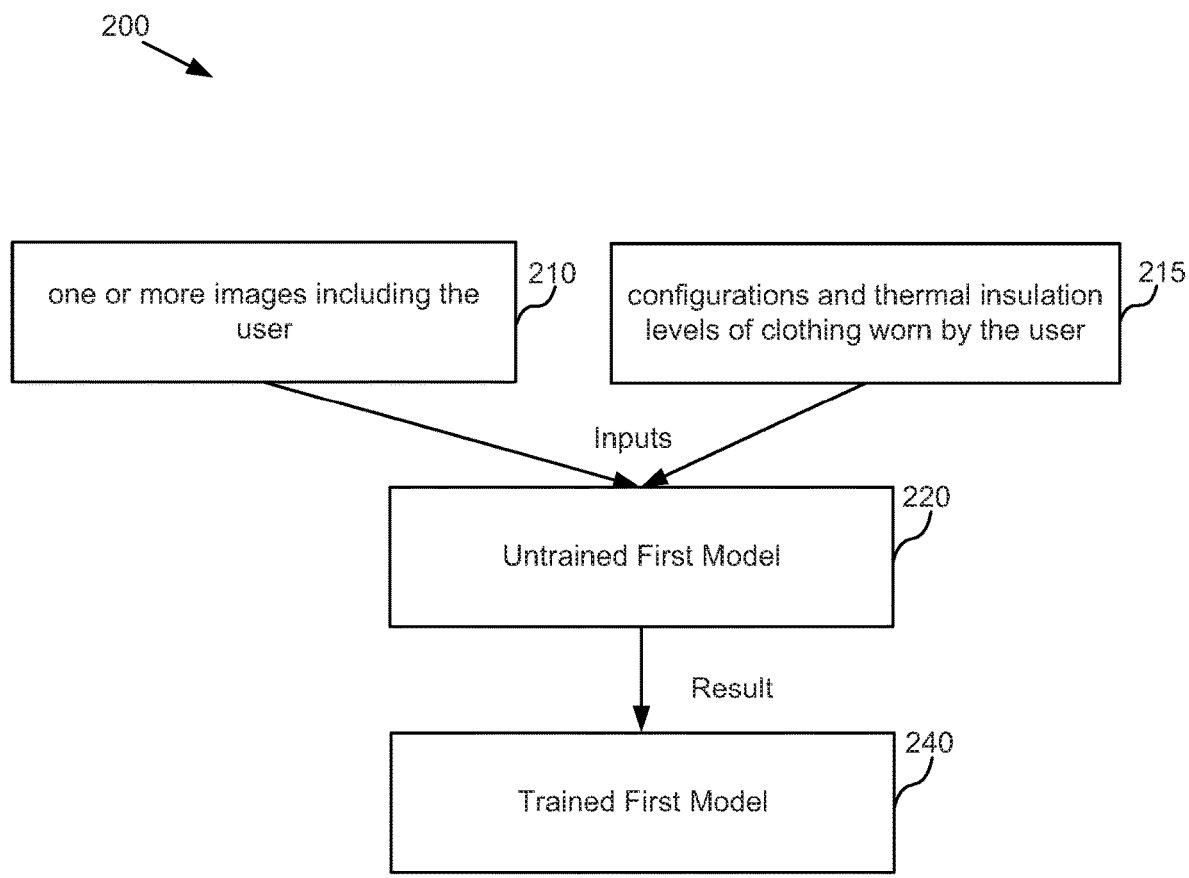
FIG. 2 is a block diagram for training a first model by inputting images including a user into the first model, according to example embodiments.

FIG. 2 is block diagram 200 for training a model according to example embodiments. The blocks or process of diagram 200 may be performed by user device 101B or system 103, although it is appreciated that any of the depicted components in figures may be employed. Diagram 200 may include structures used in the operations described for steps of FIG. 1B; that are included in structures of FIG. 1A; and/or are included in modules of FIG. 7. For example, trained first model at block 240 may include a structures that are used to perform operations described for step 415 of FIG. 4. In addition, for example, trained first model at block 240 may include structures that are used to perform operations described for step 122 of FIG. 1B; are included in determiner 112 of FIG. 1A; and/or are included in module 722 of FIG. 7.

Diagram 200 begins with one or more images of the user, and the configurations (e.g., destination and location) and thermal insulation levels of clothing worn by the user, being input into the untrained first model at block 210.

According to embodiments, the "thermal insulation levels" of clothes or clothing herein may include thermal resistance levels of the clothing worn by a person, such as the user or an individual of a crowd. The thermal insulation levels of clothes herein may include all of the clothing, the visible clothes or the external clothing shown as being worn by a person in an image. In some instances, the thermal insulation levels of clothing may include but not be limited to a thickness of each of the pieces of clothing, a material of each of the pieces of clothing, a number of layers or number of overlaying pieces of clothing and a style of each of the pieces of clothing being worn by a person in an image. In some cases, thermal insulation levels of clothes herein includes a thermal resistance level or "warmness" of the clothing shown. In some other cases, the thermal insulation levels may be levels or percentages along a linear scale from a lower level of 0 for no clothes to an upper level of 1.0 for the clothes with the highest thermal insulation level. For example, a bikini may have a thermal insulation level of 0.04 while a ski jacket, hat, gloves and boots may have a thermal insulation level of 0.98. It can be appreciated that various other linear or non-linear scales may be used to represent the thermal insulation levels herein. For example, a bell curve, logarithmic scale, linear scale from 1 to 10, alphabetic representation, or other statistical measurement may be used.

In some embodiments, at block 215 the thermal insulation levels of clothing for the one or more images may be identified by manually inputting the identifications at an input device. In other embodiments, the thermal insulation levels may be automatically identified at block 215, for example by a computer using artificial intelligence (AI), computer object recognition or a computer learning process.

The configurations at block 215 may include configurations having geographic locations, dates, times of day/night and optionally weather, such as described herein. In some cases, the configurations identified at block 215 may be identified manually, as noted for thermal insulation levels above. In some cases, the configurations may be identified automatically by a computer, such as using artificial intelligence (AI), computer object recognition or a computer learning processes. In some instances, identifying the configurations at block 215 may include data mining information or metadata from the digital data of the image/photo of the user, such as data mining photos stored on user device 101B, from a network, or from the Internet. For some embodiments, regular usage of the user device 101B or system 103 is capable of training untrained first model at block 220, using artificial intelligence (AI), computer object recognition and/or a computer learning processes.

Figure 3:
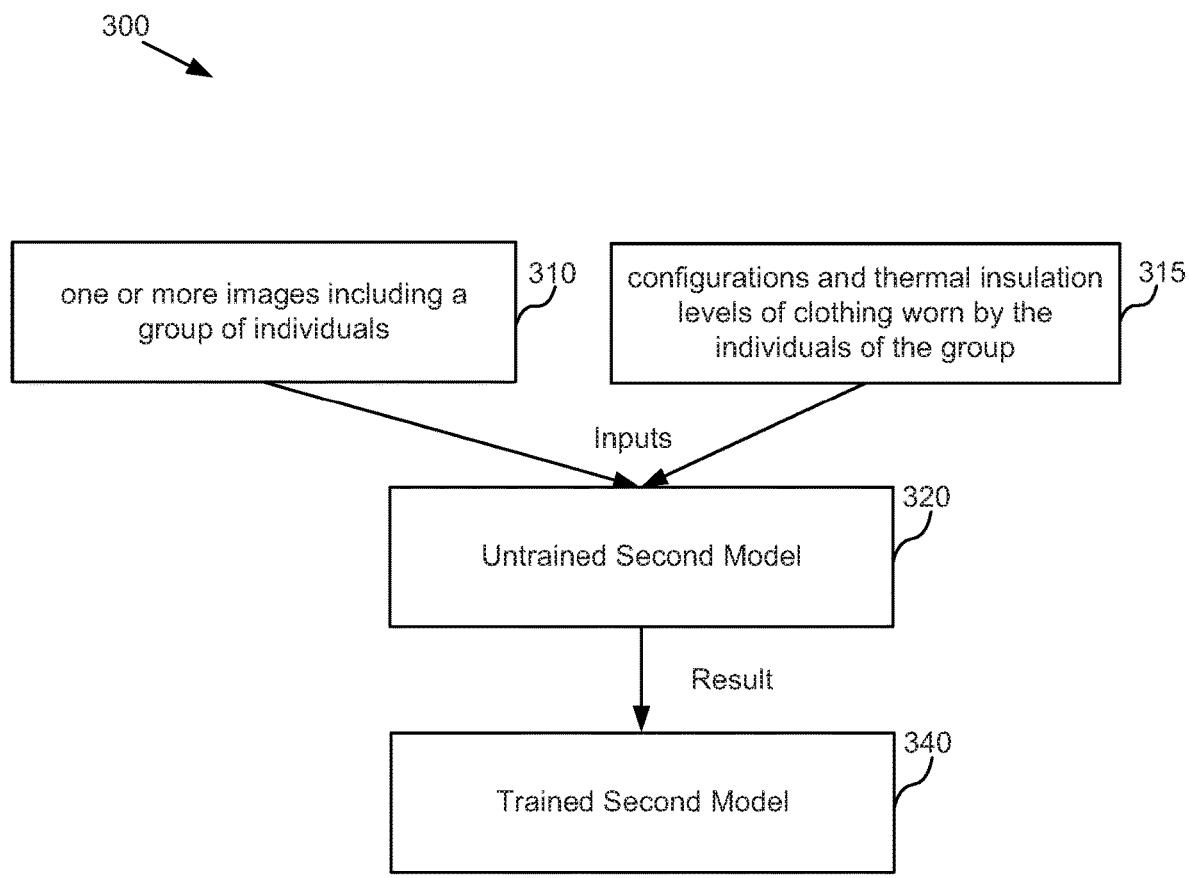
FIG. 3 is a block diagram for training a second model by inputting images including a crowd of individuals into the second model, according to example embodiments.

For some embodiments, the basic process of training a model (e.g., training untrained model at block 220 of FIG. 2 or untrained model at block 320 of FIG. 3) involves providing a model algorithm (that is, the learning algorithm) with training data to learn from, such as the images and identifications of blocks 210, 215, 310 and 315. In the examples of FIGS. 2 and 3, trained models at blocks 240 and 340 may be created by the training process.

The training data may contain the correct answer data, which is known as a target or target attribute, such as by containing the identifications from blocks 210, 215, 310 and 315. The learning algorithm finds patterns in the training data that map the input data attributes, such as the clothing shown in the input images of blocks 210 and 310 to the target (the answer that you want to predict), and it outputs a trained model that captures these patterns, such as the trained models at blocks 240 and 340.

In some instances, the basic process of training a model (e.g., training untrained model at block 220 of FIG. 2 or untrained model at block 320 of FIG. 3) involves machine learning of an algorithm of the model. As appreciated, machine learning is a type of artificial intelligence (AI) that allows software applications or algorithms to become more accurate in predicting outcomes, such as the outputs described for trained models at block 240 and 340, without being explicitly programmed. In some embodiments, machine learning can build algorithms of these models that can receive input data, such as identifications of blocks 210, 215, 310 and 315, and use statistical analysis to predict an output value of the trained models to be within an acceptable range, such as 5 to 10 percent.

Machine learning algorithms are often categorized as being supervised or unsupervised. In some instances. FIGS. 2-3 may be examples of supervised algorithms having people manually provide both input as images at blocks 210 and 310, and desired outputs as identifications of blocks 210, 215, 310 and 315 for those inputs. In addition, the people may manually furnish feedback about the accuracy of predictions performed by untrained engines at blocks 220 and 320 during training. Once training is complete, the algorithm will apply what was learned to new data, such as images or configurations input in FIGS. 1A-B and 4-6. In other instances. FIGS. 2-3 may be examples of unsupervised algorithms that do not need to be trained with desired outcome data. Instead, they use an iterative approach called deep learning to review data and arrive at conclusions, such as where identifications of blocks 210, 215, 310 and 315 are made automatically for inputs at blocks 210 and 310.

In some embodiments, configurations, such as geographic locations, dates, times of day/night and optionally weather for the images may be automatically identified at block 215, such as by a computer using artificial intelligence (AI), computer object recognition or a computer learning processes. According to embodiments, the configurations entered at 215 may be configurations entered by an algorithm or untrained first model at block 220 automatically obtaining location and time information from the input images, then automatically retrieving weather information from a database. In this case, artificial intelligence (AI), computer object recognition and/or a computer learning processes may automatically obtain location and time information from data of or associated with the images (e.g., metadata or data coded into the images), and then may automatically retrieve weather information from a weather forecast service or database.

In some embodiments, configurations automatically identified at block 215, may include a location that is the user's primary residence as determined from a shipping data, billing data, an address, a user profile, a map, or other data stored in user device 103B or on the cloud.

In other embodiments, configurations, such as geographic locations, dates, times of day/night and optionally weather for the images may be manually identified at block 215. For example, a person, expert, or administrator (e.g., of system 103) can manually input the identifications at an input device.

In some cases, inputting the images, configurations and thermal insulation levels of clothing at blocks 210 and 215 into the untrained first model at block 220 results in a trained first model at block 240. The trained first model may be able to recognize and determine relationships between the clothing worn by a user in the images, the thermal insulation level of the clothing in the images, and the configuration for the images input into the model at blocks 210 and 215. When a configuration, such as a destination, location and date, is input into this trained model at block 240, the trained model can output the thermal insulation level of clothing worn by the user for that configuration. For example, when the configuration of July 12 (date) and San Diego, Calif. (destination) is input into this trained model at block 240, the trained model may output the thermal insulation level of clothing worn by the user is 0.12. Also, in another use of the trained model, when a thermal insulation level of clothing is input to this trained model, the model can output images of clothing worn by the user that have a thermal insulation level similar to the thermal insulation level of clothing input into the trained model.

FIG. 3 is block diagram 300 for training a model by according to example embodiments. The blocks or process of diagram 300 may be performed by user device 101B or system 103, although it is appreciated that any of the depicted components in figures may be employed. Diagram 300 may include structures used in the operations described for steps of FIG. 1B; that are included in structures of FIG. 1A; and/or are included in modules of FIG. 7. For example, trained second model at block 340 may include structures that are used to perform operations described for steps 435 of FIG. 4 and 515 of FIG. 5. In addition, for example, trained second model at block 340 may include structures that are used to perform operations described for step 124 of FIG. 1B; are included in determiner 112 of FIG. 1A; and/or are included in module 722 of FIG. 7.

Similar to the diagram described above with reference to FIG. 2, the diagram 300 begins with one or more images of individuals of a crowd and the configurations (e.g., destination and location) and thermal insulation levels of clothing worn by the individuals of a crowds being input into the untrained second model at block 310.

In some embodiments, at block 315, the identification of thermal insulation levels of clothing and of configurations may be similar to those described for the configurations of block 215, such as by including manual or automatic identifications of the thermal insulation levels and configurations.

For some embodiments, regular usage of the user device 101B or system 103 is capable of training untrained second model at block 320, similar to the process noted above for training the untrained first model of block 220. In some cases, the training of the second model occurs before the user obtains or purchases the user device 101B, system 103, or a software application having the second model.

In one example embodiment, inputting the images, configurations and thermal insulation levels of clothing at blocks 310 and 315 into the untrained second model at block 320 results in a trained second model at block 340. The trained second model may be able to recognize and determine relationships between the clothing worn by an individual of the crowd in the images, the thermal insulation level of the clothing in the images, and the configuration for the images input into the model at blocks 310 and 315. When a configuration, such as a destination location and date, is input into this trained model at block 340, the trained model can output the thermal insulation level of clothing worn by the crowd or an individual of the crowd for that configuration. For example, when the configuration of May 22 (date) and San Jose, Calif. (destination) is input into this trained model at block 340, the trained model may output the thermal insulation level of clothing worn by the crowd or an individual of the crowd is 0.41. Also, in another use of the trained model, when a thermal insulation level of clothing is input to this trained model, the model can output images of clothing worn by an individual of the crowd that have a thermal insulation level similar to the thermal insulation level of clothing input into the trained model. The trained model may also have information or links to vendor websites that identify the clothing in the image and where to purchase the clothing.

Figure 4:
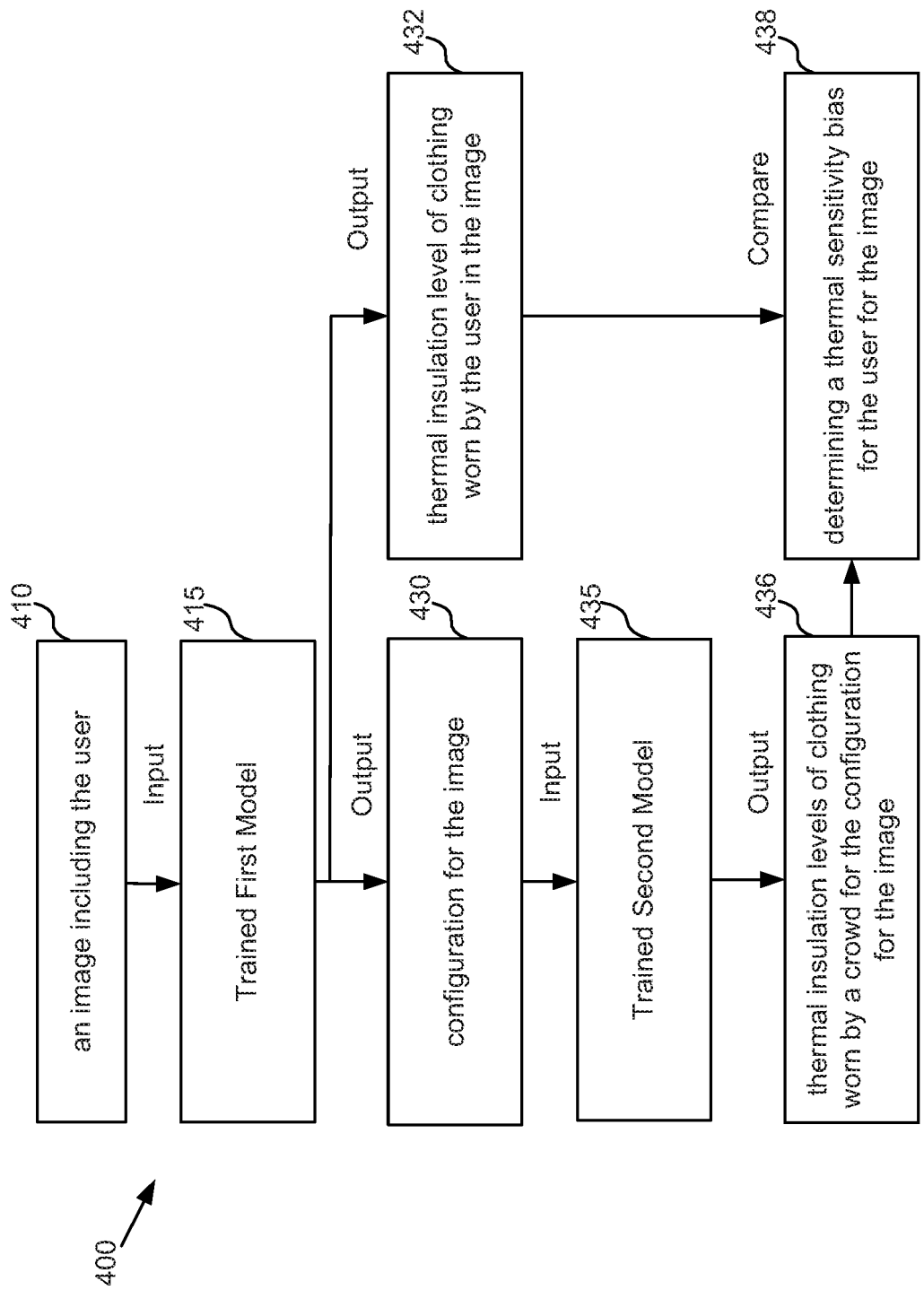
FIG. 4 is a block diagram for determining a thermal sensitivity bias according to example embodiments.

FIG. 4 is block diagram 400 for determining a thermal sensitivity bias according to embodiments of the disclosure. The thermal sensitivity bias for the user may be determined, for example, by comparison of the thermal insulation level of clothing worn by the user to the thermal insulation level of clothing worn by the crowd at the same configuration. The blocks or process of block diagram 400 may be performed by user device 101B or system 103, but are not limited to such components. Diagram 400 may include structures used in the operations described for steps of FIG. 1B; that are included in structures of FIG. 1A; and/or are included in modules of FIG. 7. For example, blocks 410, 415 and 432 may include structures that are used to perform operations described for step 122 of FIG. 1B. Also, for example, blocks 430, 435 and 436 may include structures that are used to perform operations described for step 124 of FIG. 1B. In addition, for example, block 438 may include structures that are used to perform operations described for steps 126 and 132 of FIG. 1B; are included in determiner 112 and generator 116 of FIG. 1A; and/or are included in modules 722 and 726 of FIG. 7.

At block 410, an image depicting the user is input into the trained first model at block 415. In some embodiment, at block 410, an image is input into the trained model at block 415, where the trained model may be the trained model referenced above in block 240 of FIG. 2. For example, an image of a user wearing a fur coat while on vacation in Italy is used as an input into a trained first model.

When the image is input into trained first model at block 415, the trained first model outputs the configuration for the image at block 430. For example, the model may output the configuration of Sienna Italy (destination), January 12 (date), with slightly colder than normal weather for that time of year. The configuration output at block 430 is then input into the trained second model at block 435. In one embodiment, a configuration is input into the trained second model at block 435, where the trained second model may be the trained second model at block 340 of FIG. 3.

When the configuration is input into trained second model at block 435, the model outputs the thermal insulation level of clothing worn by the crowd for that configuration at block 436. For example, the model may output the thermal insulation level of clothing worn by the crowd is 0.75.

At block 432, the trained first model also outputs the thermal insulation level of clothing worn by the user corresponding to the image. For example, the trained model may output that the thermal insulation level of clothing worn by the user is 0.86.

At block 438, the thermal insulation level of clothing worn by the crowd for the configuration at block 436 is compared to the thermal insulation level of clothing worn by the user at block 432. In one example, by comparing the two outputs at blocks 432 and 436, the thermal sensitivity bias for the user may be calculated by subtracting the thermal insulation level of clothing worn by the crowd at block 436 from the thermal insulation level of clothing worn by the user at block 432. For example, the thermal sensitivity bias for the user is calculated by subtracting the thermal insulation level of clothing worn by the crowd (0.75) from the thermal insulation level of clothing worn by the user (0.86), which results in a thermal sensitivity bias for the user of 1.1.

In another embodiment, the process includes inputting multiple images into the model at block 415, inputting multiple configurations for the images into the trained model at block 435, and comparing multiple outputs from block 436 and block 432 to determine multiple thermal sensitivity biases for the user at block 438. The multiple thermal sensitivity biases from comparisons at block 438 can be averaged to determine the thermal sensitivity biases that is the average bias for the user based on the input images. It can be appreciated that instead of an average, another mathematical combination such as using least squares or the like can be used to determine the bias.

In some cases, the images for 122-124 and block 410 include the user and the crowd in each of a number of various images. In other cases, the images for 122-124 and block 410 include the user and the crowd in various different images of the one or more images, but those various different images were taken at a same time of year or date and at the same location.

Figure 5:
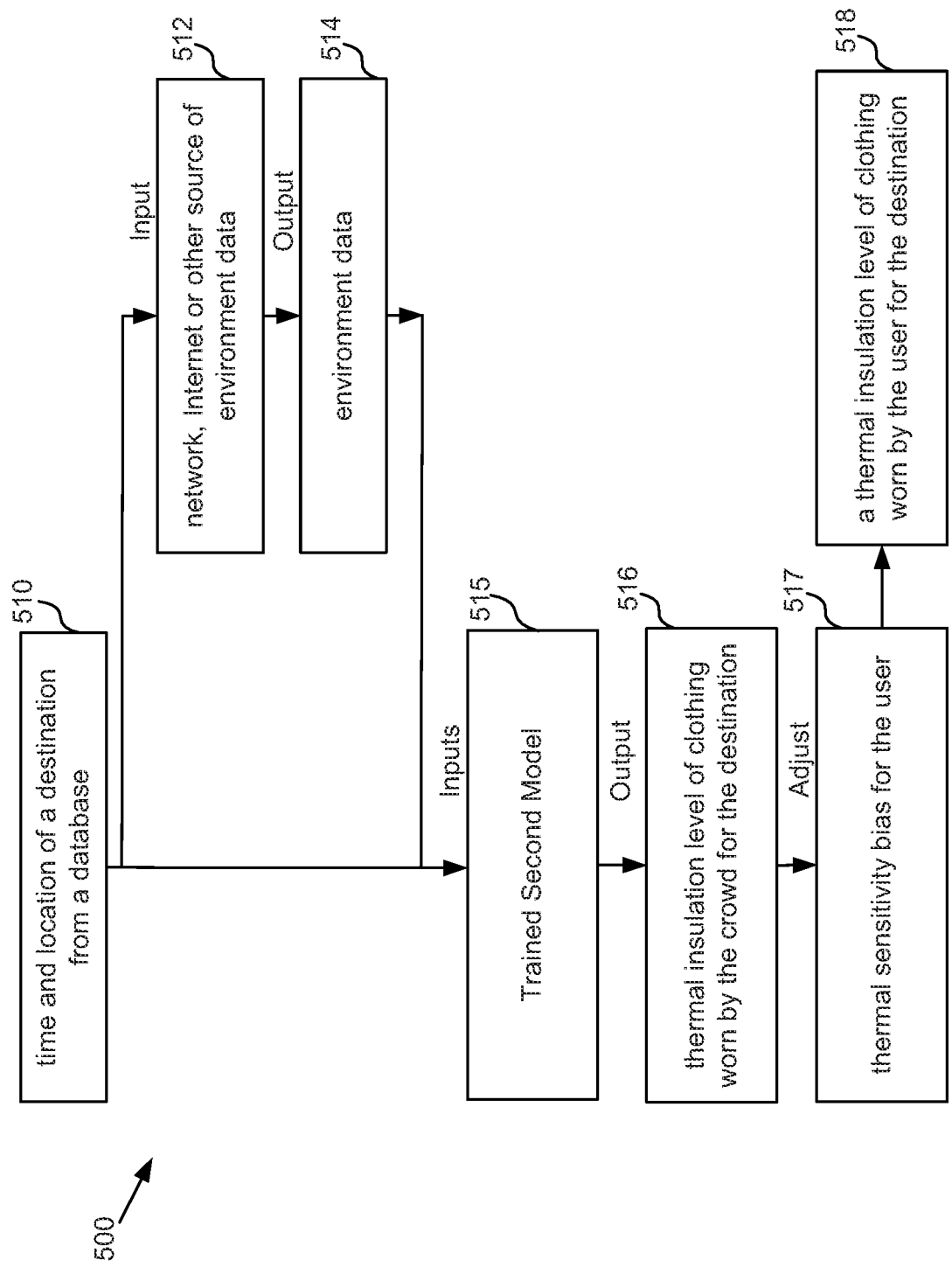
FIG. 5 is a block diagram for generating a thermal insulation level of clothing worn by the user for a destination, according to example embodiments.

FIG. 5 is block diagram 500 for generating a thermal insulation level of clothing worn by the user at a destination according to example embodiments. The blocks or process of diagram 500 may be performed by user device 101B or system 103, but are not limited to such components. Diagram 500 may include structures used in the operations described for steps of FIG. 1B; that are included in structures of FIG. 1A; and/or are included in modules of FIG. 7. For example, blocks 510, 512 and 514 may include structures that are used to perform operations described for step 128 of FIG. 1B. Also, for example, blocks 510, 515 and 516 may include structures that are used to perform operations described for step 130 of FIG. 1B; are included in predictor 114 of FIG. 1A; and/or are included in module 724 of FIG. 7. Also, for example, blocks 516 and/or 518 may include structures that are used to perform operations described for step 132 of FIG. 1B; are included in generator 116 of FIG. 1A; and/or are included in module 726 of FIG. 7.

At block 510, a time and location of a destination is input into trained second model at block 515. The time and location information may be retrieved from user input or based on a trip itinerary of the user. The data itself may be stored in storage or a storage system, such as a database or datacenter. The retrieved time and location information is then used to retrieve environmental data at the destination, for example, by accessing a network, Internet or other source of environment data at block 512. For example, the environment data may be retrieved via a network communicatively coupled to a weather center at the designation. It is also appreciated that the time may be a single or range of date(s) of a year, and the location may be a geographic location.

In some embodiments, at block 510 a configurations automatically input that includes a location that is not the user's primary residence.

In one example embodiment, when the time and location of the destination is retrieved, the environment data for the destination is output at block 514. For example, if the time is December 15 and the location is Seattle, Wash. is input at block 512, a temperature=24 degrees F., wind=12 mph, and humidity=45 percent may be output at as the environment data at block 514. Subsequently, the environment data output at block 514 may be input into the trained second model at block 515.

In one embodiment, the trained second model in block 515 may be the trained second model in block 340 (FIG. 3). When the time and location at block 510 and the environment data output at block 514 are input into the trained second model, the trained second model outputs a thermal insulation level of clothing worn by the crowd for the destination at block 516. For example, if the time is December 15 and the location is Seattle, Wash. is input at block 512, a temperature=24 degrees F., wind=12 mph, and humidity=45 percent may be output at as the environment data at block 514. Based on the time and location, and the environment data, as input into the trained second model, the trained second model may output a thermal insulation level of clothing worn by the crowd at block 516. For example, the thermal insulation level may be identified by a number or percentage, such as 0.91.

At block 517, the thermal insulation level of clothing worn by the crowd is adjusted by the thermal sensitivity bias for the user (block 438 of FIG. 4 or at 126 of FIG. 1B). In one instance, the thermal insulation level of clothing worn by the crowd for the destination adjusted by the thermal sensitivity bias is output at block 518 as the thermal insulation level of clothing worn by the user for the destination.

In one embodiment, adjusting the thermal insulation level by the thermal sensitivity bias may include adding the thermal sensitivity bias for the user at block 438 (FIG. 4) to the thermal insulation level of the clothing worn by the crowd at block 516. It can be appreciated that other adjustments may be considered, including using least squares or adding a portion of the thermal insulation level output at block 438 or at 126 of FIG. 1B to the thermal insulation level output at block 516.

In other embodiments, the thermal insulation level output at block 516 may be determined based on a range of factors. For some embodiments, the range of factors may be a range in the input data of block 510 and/or block 514. For example, if an itinerary is created for travel to Toronto on November 10th, the thermal insulation level may not only consider the specific date and location in the itinerary, but may also consider ranges outside of Toronto (e.g., 50 or 60 km radius outside of Toronto), or different dates (e.g., November 9th and 12th).

In some embodiments, the thermal insulation level output at block 516 may be determined based on environment data at block 514, such as based on weather temperature, rather than including being based on destination location and date of block 510. For example, if it is a warm winter for the current year, and it is 10 degrees F. warmer than it was for the prior year, the thermal insulation level output at block 516 may be determined based on the thermal insulation level of clothing for local Toronto people based on temperature rather than the date/time.

For some embodiments, the thermal insulation level output at block 516 may be determined based on a range in temperature difference from the environment data at block 514. For example, a temperature range of 3-5 degrees F. difference from the weather forecast of block 514 may be input to block 516. In this case, the output at block 516 may be the the thermal insulation level for clothing worn on October 10, in Toronto rather than clothing worn on November 10 in Toronto. In these cases, the user may also be warned that "this is how local people normally dress like, but due to the special weather this year, this is what we recommend."

FIG. 6 is a flow diagram for identifying an image with clothing having a specified thermal insulation level according to example embodiments. In one embodiment, the depicted process identifies an image of clothing from a database having a thermal insulation level comparable to a thermal insulation level of clothing worn by the user for a destination. Process 650 may be performed by user device 101B or system 103, but is not limited thereto.

At 652, the thermal insulation level of clothing worn by the user for the destination at 132 or at 518 is matched to a thermal insulation level of clothing worn by the user in an image, such as the thermal insulation level depicted in an image of the user. In other instances, this database may store results of the trained model, where the trained model is a dressing style model that is a personal stylish model for the user, such as trained using the images input at block 210. In one embodiment, the images of the user may be considered a user profile, such as a profile based on clothing from the user's existing wardrobe or that has a style typically worn by the user. For example, when a thermal insulation level of clothing worn by the crowd of 0.91 is input into a model that is trained using the images input at block 210, the trained model may output an image of the user wearing a fur coat, fur hat and boots. Since this model was trained using images input at block 210, the image of the user that is output by the model may be considered a personal style or a user profile of the user. In some embodiments, after there is a match at 652, the process may continue to 654 and/or 656 to determine if there is an additional match at 654 and/or 656.

At 654, the thermal insulation level of clothing worn by the user for the destination at 132 or at 518 is matched to a thermal insulation level of clothing worn by the crowd in an image, such as the thermal insulation level depicted in an image of the crowd. In other instances, this database may store results of the trained model, where the trained model is a dressing style model that is a location stylish model for the crowd, such as trained using the images input at block 310. In one embodiment, the images of the clothing worn by an individual of a crowd may be considered a "dress code" for the destination, such as clothes typically worn at by a crowd at the destination. In some cases, it may be considered a local style of clothing of people that reside at a location of the destination. For example, when a thermal insulation level of clothing worn by the crowd of 0.91 is input into a model that is trained using the images input at block 310, the database may output an image of an individual of a crowd wearing a fur coat and boots. Since this model was trained using images input at block 310, the image of the individual that is output by the model may be considered a local style or a dress code of the location of the destination.

In some embodiments, after there is a match at 654, the process may continue to 656 to determine if there is an additional match at 656. For example, in one embodiment, the thermal insulation level of clothing worn by the user may match a thermal insulation level of clothing worn in more than one image at 652 or 654. In this case, if one of the matches is for thermal insulation level of clothing in an image from the dressing style models, user device 101B or system 103 will display the image from the dressing style model that is the personalized stylish model for the user or the location stylish model for the crowd instead of displaying another image having clothing with a thermal insulation level that matches.

In another example, a "style" of clothing may be based on the type of clothing the user or an individual in a crowd wears in the images input at block 210 or 310, such as clothing that includes a long sleeve sweatshirt with a hood (e.g., a "hoodie"). One such example, for a destination location of Hawaii during the summer, a style of clothing that an individual in a crowd wears in the images input at block 310, may be a long sleeve rash guard worn in the swimming pool, which can be a big style difference from regular swimwear or a bikini.

At 656, the thermal insulation level of clothing worn by the user for the destination is matched against the thermal insulation level of clothing in an image from a vendor, such as in an image of database 104B or on server 104A. In one embodiment, the thermal insulation level of clothing worn by the user is matched with the thermal insulation level of clothing worn by an individual in one or more images used by the vendor 104 (FIG. 1) for marketing or sales of those clothes.

In one instance, the thermal insulation level of clothing worn by the user may match a thermal insulation level of clothing worn in more than one image at 652, 654 and/or 654. In this case, if one of the matches is for the thermal insulation level of clothing in an image from a vendor, user device 101B or system 103 will display the image clothing in an image from a vendor instead of displaying another image having clothing with a thermal insulation level that matches.

The images from the vendor 104 may be part of data content, such as files, images, videos, and the like. The vendor 104 may provide (e.g., be a "producer" of) images of clothing matching the thermal insulation level of clothing worn by the user for the destination. This image of clothing from the vendor 104 may be considered a sales or marketing attempt, such as to make a suggestion of clothes for the user to buy from the vendor 104. For example, when a thermal insulation level of clothing worn by the crowd of 0.91 generated at 132 is input at 134, the resulting output may be an image of a fashion model wearing a fur coat and boots sold by the vendor 104, including the name and price of the items and a hyperlink to see more details of and/or purchase those items.

If it is determined at 652, 654 or 656 that a match is found between the thermal insulation level of the crowd and the user, the clothing identified in the image may be displayed to the user by user device 101B, system 103 or server 104A on a display of user device 101B. Displaying the image may include, for example, recommending a style of clothing to the user using, for example, a computer or mobile device based on the identified image (e.g., see 136 of FIG. 1B).

In some embodiments, the image of clothing worn by an individual (652), a crowd (654) and/or in an image of clothing from a clothing vendor (656) may include a description of the clothing, such as identifying the name or identification of the piece(s) of clothing worn as well as a manufacturer, distributor, retailer store, or vendor from whom the clothing can be purchased. This image may also include a link (e.g., hyperlink) that can connect the user device to the vendor 104, such as by presenting an interface capability for the user 101 to purchase the clothing in the image from the vendor's website using user device 101B. After the purchase, the vendor 104 can ship the clothing in the image recommended to the user so that it can be worn for or at the destination, such as of 128 or block 510. This can create additional business, a good business model, and increased profits for the vendor 104.

As noted above, various structures of FIGS. 2-5 may be used to perform the operations described for steps of FIG. 1B. Looking at it from another perspective, the steps of FIGS. 1B and 6 may include operations performed by structures of FIGS. 1A, 2-5 and 7. For example, step 122 of FIG. 1B may include operations performed by structures described for blocks 410, 415 and 432 of FIG. 4; and for blocks 210-240 of FIG. 2 which support how to train the first model which is used in block 415. Also, for example, step 124 of FIG. 1B may include operations performed by structures described for blocks 430, 435 and 436 of FIG. 4; and for blocks 310-340 of FIG. 3 which support how to train the second model which is used in block 415. Next, for example, step 126 of FIG. 1B may include operations performed by structures described for determiner 112 of FIG. 1A; block 438 of FIG. 4; and/or for module 722 of FIG. 7. In addition, for example, step 128 of FIG. 1B may include operations performed by structures described for blocks 510, 512 and 514 of FIG. 5. Also, for example, step 130 of FIG. 1B may include operations performed by structures described for predictor 114 of FIG. 1A; for blocks 510, 515 and 516 of FIG. 5; for blocks 310-340 of FIG. 3 which support how to train the second model which is used in block 515; and/or for module 724 of FIG. 7. Next, for example, step 132 of FIG. 1B may include operations performed by structures described for generator 116 of FIG. 1A; for blocks 516, 438 and 518 of FIGS. 4-5; and/or for module 726 of FIG. 7. Also, for example, step 134 of FIG. 1B may include operations performed by structures described for identifier 118 of FIG. 1A; and/or for module 728 of FIG. 7. Next, for example, steps 652, 654 and 656 of FIG. 6 may include operations performed by structures described for identifier 118 of FIG. 1A; and/or for module 728 of FIG. 7.

An example of recommending a style of clothing to a user will now be discussed with reference to FIGS. 1-5. This example is for illustration purposes only, and is a specific application of certain embodiments described herein. This example may be for or include determining thermal insulation levels for clothing at a computer or mobile device, such as described herein. This example presumes that the first and second models have been trained according to FIGS. 2-3. The steps or components of this example may be performed by user device 101B or system 103, but are not limited to such components.

In the example, an image of the user is input into the trained first model at block 415, where the image is a photo of person wearing pants, shoes, a shirt and a sweater at a specific geographic location and time.

After the image is input at block 415, the trained first model outputs, at block 430, a configuration of the image with a geographic location=San Jose, Calif.; date=June 1 (current year); time of day=8 am PST; and may optionally output temperature=80 degrees Fahrenheit; relative humidity=50 percent; wind=10 miles per hour (mph). The trained first model also outputs, at block 432, a thermal insulation level of clothing worn in the image by the user having Personal Warmness=0.55.

The configuration is then input, at block 430, into a trained second model at block 435, and the trained second model outputs the thermal insulation level of clothing worn by the crowd in the image for the output configuration as Crowd Warmness=0.48 (at 436).

At block 438, the thermal insulation level of clothing of the crowd=0.48 is compared to the thermal insulation level of clothing of the user=0.55. The thermal sensitivity bias for the user is calculated by subtracting the level of clothing worn by the crowd (0.48) from the level of clothing worn by the user (0.55), which is equal to a sensitivity bias of 0.07. In one embodiment, when multiple thermal sensitivity biases exist, the bias may be averaged to determine an average thermal sensitivity biases for the user.

In one example, the average bias for this user is Personal Sensitivity Bias=avg(sensitivity bias)=0.08. This average bias is greater than the bias for the user calculated to be 0.07 calculated above at block 438 for a single image.

The example continues to block 510 (FIG. 5), where a time and location of a destination is input into the trained second model (block 515) and into a network or another source of environment data (block 512). For example, the destination and/or configuration input at block 510 may be a geographic location=Toronto, Canada; time or date=November 1 (current year); and time of day=7:12 pm PST.

After the destination and/or configuration is input into the trained second model at block 510, block 514 outputs environment data for the input destination and/or configuration such that temperature=9 digress Celsius; relative humidity=84 percent; wind=13 kilometer per hour (km/h).

At block 515, the time and location of the destination is input from block 510, and the environment data is input from block 514 into the trained second model. The trained second model outputs, at block 516, the thermal insulation level of clothing worn by the crowd for the destination as Crowd Warmness=0.84.

At block 517, the thermal insulation level 0.84 of clothing worn by the crowd output at block 516 is adjusted by the average thermal sensitivity bias for the user of 0.08 (block 438). The adjusting adds the thermal sensitivity level 0.84 to the bias of 0.08 to calculate the thermal insulation level of clothing worn by the user for the destination as 0.92. In other words, the adjusting at block 517 is 0.08 (Sensitivity Bias–

Average) of block 517+0.84 (Crowd Warmness of block 516 and outputs=0.92 (Personalized trip warmness) of block 518.

It is noted that in this example, the destination (Toronto) may be a geographic location that the user had not visited before, or may be a location the user has visited but on another date (November 1). Thus, the level output at block 518 may be very helpful in ensuring the user brings the proper thermal level clothing to the destination based on the specific configuration.

Next, the example may continue to 652 (FIG. 6) to identify an image in which clothing with a thermal insulation level is comparable to the thermal insulation level of clothing worn by the user at the destination. For example, the personalized trip warmness may equal 0.92, which is comparable to boots, pants, and a heavy jacket with a hood.

Next, the example may continue to 654 and 656 (FIG. 6) but not be able to identify an image in which clothing with a thermal insulation level is comparable to the thermal insulation level of clothing worn by the user at the destination at 654 or 656.

The example may continue to 136 (FIG. 1A or 6) to recommend a style of clothing to the user based on the identified image. For example, user device 101B may display to the user an image of the user wearing boots, pants, and a heavy jacket with a hat and the text "You should wear this on your trip to Toronto, Canada on November 1."

By determining a thermal sensitivity bias for thermal insulation levels of clothes worn by a user and generating of a thermal insulation level of clothing recommended to be worn by the user at a later destination and date, the present technology can provide many benefits. For example, embodiments are able to use a smart algorithm or computer models to learn dressing profiles from previous pictures of the user (e.g., see FIG. 2) or individuals of a crowd (e.g., see FIG. 3) and based on these, give the user personalized dressing recommendations based on destination and weather, typical clothes worn at by a crowd for the destination, and a user profile of clothing (e.g., see FIGS. 1B and 4-6). These personalized dressing recommendations can clothing identified an image from the database that has the thermal insulation level of clothing recommended to be worn by the user at a later destination, such as noted at 136 in the example above.

Another benefit is that the embodiments can be implemented in an algorithm or models that are running in the background of a user device or system, without the need for user input. In one example, regular usage of user device 101B or system 103 is capable of training the algorithm (e.g., first model as shown in FIG. 2 and optionally second model as shown in FIG. 3) such as based on or by data mining of images stored on the user device, and optionally images accessible from the user device, such as using a network or the Internet.

Thus, the embodiments described herein can provide a more accurate, efficient and intuitive way to determine what clothing is appropriate at a future date or destination to be traveled to, such as by recommending clothing. The appropriate clothing can have a proper level of thermal insulation for destinations and dates having temperature and weather that is different from what a person is currently experiencing or has experienced. The appropriate clothing can then be purchased, packed and/or worn at the destinations and dates.

Figure 7:
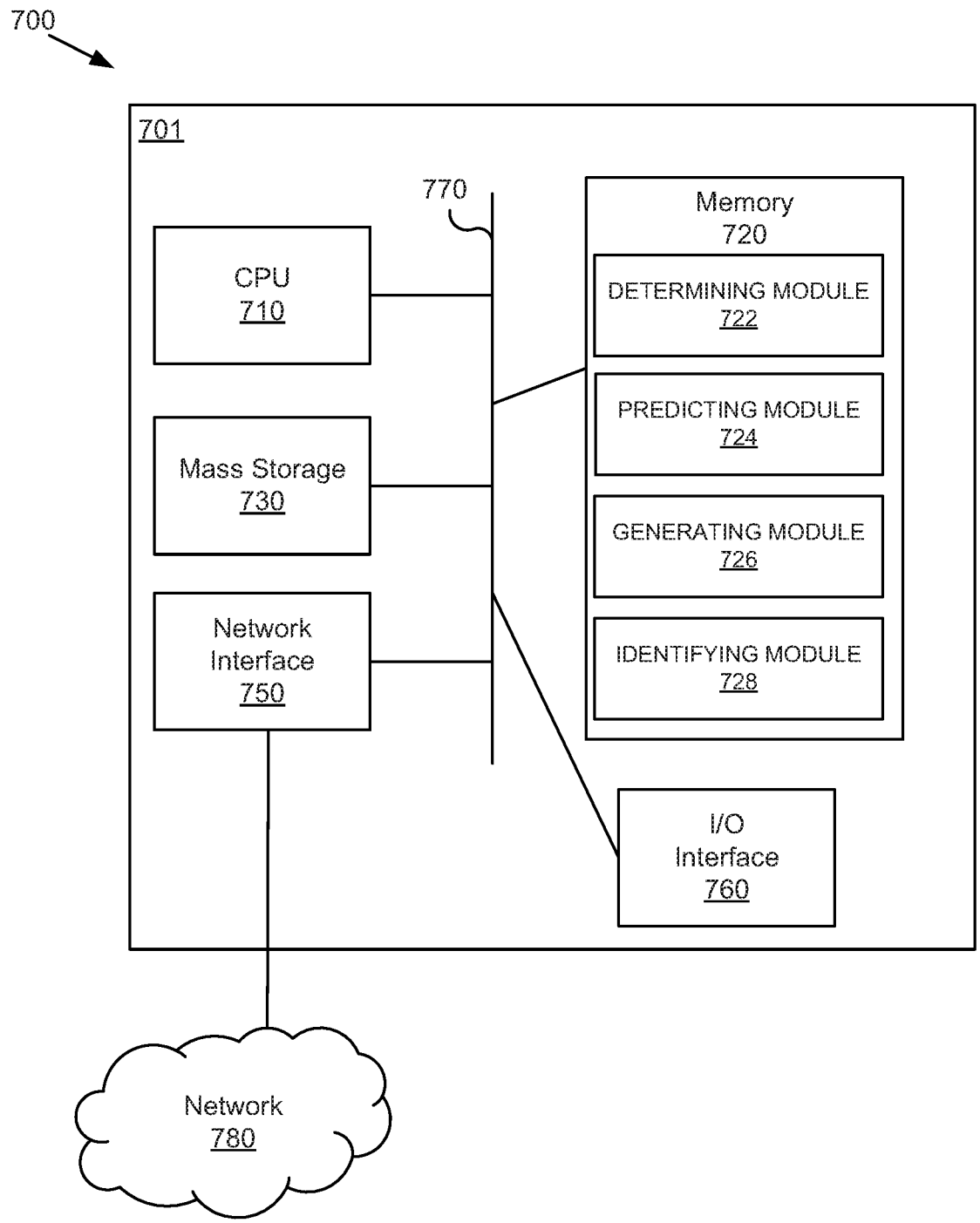
FIG. 7 is a block diagram of a network system that can be used to implement various embodiments.

FIG. 7 is a block diagram of a device 700 that can be used to implement various embodiments. In some cases, device 700 is or is included in user device 101A or 101B. Specific devices may utilize all of the components shown, or a subset of the components, and levels of integration may vary from device to device. Furthermore, the device 700 may contain multiple instances of a component, such as multiple processing units, processors, memories, transmitters, receivers, etc. The device 700 may comprise a processing unit 701 equipped with one or more input/output devices, such as network interfaces, storage interfaces, and the like. The processing unit 701 may include a central processing unit (CPU) 710, a memory 720, a mass storage device 730, and an I/O interface 760 connected to a bus 770. The bus 770 may be one or more of any type of several bus architectures including a memory bus or memory controller, a peripheral bus or the like.

The CPU 710 may comprise any type of electronic data processor. The memory 720 may comprise any type of system memory such as static random access memory (SRAM), dynamic random access memory (DRAM), synchronous DRAM (SDRAM), read-only memory (ROM), a combination thereof, or the like. In an embodiment, the memory 720 may include ROM for use at boot-up, and DRAM for program and data storage for use while executing programs. In embodiments, the memory 720 is non-transitory.

In some embodiments, the memory 720 includes a determining module 722 for determining a thermal sensitivity bias for the user 101, such as performed according to descriptions of FIGS. 1A-6. Here determining the thermal sensitivity bias may include: (1) analyzing a thermal insulation level of clothing worn by a user in one or more images including a user and a crowd of individuals; (2) analyzing a thermal insulation level of clothing worn by the crowd in the one or more images; and then (3) determining the thermal sensitivity bias for the user by comparison of the thermal insulation level of clothing worn by the user at to the thermal insulation level of clothing worn by the crowd.

In some embodiments, the memory 720 includes a predicting module 724 for predicting a thermal insulation level of clothing worn by the crowd, such as performed according to descriptions of FIGS. 1A-6. Here, predicting the thermal insulation level may include (1) collecting environment data based on at least one of time and location of a destination from a database; and then (2) predicting a thermal insulation level of clothing worn by the crowd for the destination based on the destination and collected environment data.

In some embodiments, the memory 720 includes generating module 726 for generating a thermal insulation level of clothing worn by the user for the destination, such as performed according to descriptions of FIGS. 1A-6. Here, generating may include generating a thermal insulation level of clothing worn by the user for the destination comprised of the thermal insulation level of the clothing worn by the crowd for the destination (e.g., as predicted by predicting module 724) adjusted by the thermal sensitivity bias for the user (e.g., as determined by determining module 722 above).

In some embodiments, the memory 720 includes an identifying module 728 for identifying an image from a database having clothing, such as performed according to descriptions of FIGS. 1A-6. Here, identifying may include identifying an image from the database having clothing with a thermal insulation level comparable to the thermal insulation level of clothing worn by the user for the destination (e.g., as generated by generating module 726 above). Here, identifying may also include recommending a style of clothing to the user using a computer or mobile device based on the identified image (e.g., as identified by identifying module 728).

The mass storage device 730 may comprise any type of storage device configured to store data, programs, and other information and to make the data, programs, and other information accessible via the bus 770. The mass storage device 730 may comprise, for example, one or more of a solid state drive, hard disk drive, a magnetic disk drive, an optical disk drive, or the like.

The processing unit 701 also includes one or more network interfaces 750, which may comprise wired links, such as an Ethernet cable or the like, and/or wireless links to access nodes or one or more networks 780, which may be network 102. The network interface 750 allows the processing unit 701 to communicate with remote units via the networks 780. For example, the network interface 750 may provide wireless communication via one or more transmitters/transmit antennas and one or more receivers/receive antennas. In an embodiment, the processing unit 701 is coupled to a local-area network or a wide-area network for data processing and communications with remote devices, such as other processing units, the Internet, remote storage facilities, or the like.

Further, in an exemplary, non-limited embodiment, implementations can include distributed processing, component/object distributed processing, and parallel processing. Virtual computer system processing can be constructed to implement one or more of the methods or functionalities as described herein, and a processor described herein may be used to support a virtual processing environment. Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

Some embodiments herein may be implemented in computer-readable non-transitory media that includes all types of computer readable media, including magnetic storage media, optical storage media, and solid state storage media and specifically excludes signals. It should be understood that the software can be installed in and sold with the determining module 722, predicting module 724, generating module 726 and identifying module 728 (optional). Alternatively the software can be obtained and loaded into the determining module 722, predicting module 724, generating module 726 and identifying module 728 (optional), including obtaining the software via a disc medium or from any manner of network or distribution system, including, for example, from a server owned by the software creator or from a server not owned but used by the software creator. The software can be stored on a server for distribution over the Internet, for example.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

For purposes of this document, each process associated with the disclosed technology may be performed continuously and by one or more computing devices. Each step in a process may be performed by the same or different computing devices as those used in other steps, and each step need not necessarily be performed by a single computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A method for determining thermal insulation levels for clothing at a computer or mobile device, comprising:
analyzing a thermal insulation level of clothing worn by a user in one or more images including the user and a crowd of individuals;
analyzing a thermal insulation level of clothing worn by the crowd of individuals in the one or more images;
determining a thermal sensitivity bias for the user by averaging multiple comparisons of the thermal insulation level of clothing worn by the user to thermal insulation levels of clothing worn by the crowd at a same time, location, and environment;
collecting environment data based on at least one of time and location of a destination from a database;
predicting the thermal insulation level of clothing worn by the crowd for the destination based on the destination and the collected environment data;
generating the thermal insulation level of clothing worn by the user at the destination comprised of the thermal insulation level of the clothing worn by the crowd for the destination adjusted by the thermal sensitivity bias for the user;
identifying an image from the database having clothing with the thermal insulation level comparable to the thermal insulation level of clothing worn by the user at the destination; and
recommending a style of clothing to the user using a computer or mobile device based on the identified image.

2. The method of claim 1, further comprising:
collecting past environment, time and location data from one or more images including the user and/or a crowd of individuals; and
correlating the past environment, time and location data to the thermal insulation level of clothing worn by the user or crowd of individuals in the same image.

3. The method of claim 1, wherein:
the one or more images include the user in each of a plurality of the one or more images;
the one or more images include the crowd of individuals in each of a plurality of the one or more images; or
the one or more images include the user and the crowd of individuals at a same location and at the same time of year in each of a plurality of the one or more images.

4. The method of claim 1, wherein:
analyzing the thermal insulation level of clothing worn by the crowd includes inputting the one or more images including the crowd into a trained second model,
analyzing the thermal insulation level of clothing worn by the user includes inputting the one or more images including the user into a trained first model, and
predicting the thermal insulation level of clothing worn by the crowd at the destination includes inputting the destination and collected environment data into the trained second model.

5. The method of claim 1, wherein identifying an image from the database comprises one of:
matching the thermal insulation level of clothing worn by the user at the destination with the thermal insulation level of clothing worn by the user in the one or more images including the user;
matching the thermal insulation level of clothing worn by the user at the destination with the thermal insulation level of clothing worn by the crowd in the one or more images including the crowd; or
matching the thermal insulation level of clothing worn by the user at the destination with a thermal insulation level of clothing in an image from a vendor.

6. The method of claim 5, further comprising displaying the image from the vendor to the user, wherein the image from the vendor has a link to a website of the vendor, the website being capable of selling the clothing in the image from the vendor to the user.

7. The method of claim 5, wherein recommending a style of clothing to the user includes one of displaying the matched clothing worn by the user in the one or more images including the user, or displaying the matched clothing in the image from a vendor when the clothing in the image from a vendor was previously viewed at a website of the vendor.

8. The method of claim 1, wherein the database comprises average thermal insulation levels of clothing worn by the crowd in a plurality of locations, times of year and environments.

9. The method of claim 1, wherein:
the destination includes one of a trip itinerary, or a trip time and location;
the collected environment data includes weather information for the destination; and
the destination is at a different location than a location of the user's primary residence.

10. A device for determining thermal insulation levels for clothing device, comprising:
a memory storage comprising instructions; and
one or more processors in communication with the memory storage, wherein the one or more processors execute the instructions to:
determine a thermal sensitivity bias for a user by averaging multiple comparisons of the thermal insulation level of clothing worn by the user to thermal insulation levels of clothing worn by a crowd of individuals in the one or more images at a same time, location, and environment;
collect environment data based on at least one of time and location of a destination from a database;
predict the thermal insulation level of clothing worn by the crowd for the destination based on the destination and the collected environment data;
generate the thermal insulation level of clothing worn by the user at the destination comprised of the thermal insulation level of the clothing worn by the crowd for the destination adjusted by the thermal sensitivity bias for the user; and
identify an image from the database having clothing with the thermal insulation level comparable to the thermal insulation level of clothing worn by the user at the destination.

11. The device of claim 10, wherein:
the one or more images include the user in each of a plurality of the one or more images;
the one or more images include the crowd of individuals in each of a plurality of the one or more images; or
the one or more images include the user and the crowd of individuals at a same location and at the same time of year in each of a plurality of the one or more images.

12. The device of claim 10,
wherein determine the thermal sensitivity bias for the user includes:
inputting the one or more images including the crowd into a trained second model to determine the thermal insulation level of clothing worn by the crowd in the one or more images; and
inputting the one or more images including the user into a trained first model to determine the thermal insulation level of clothing worn by the user in one or more images including the user and a crowd of individuals to; and
wherein predicting the thermal insulation level of clothing worn by the crowd at the destination includes inputting the destination and collected environment data into the trained second model.

13. The device of claim 10, wherein identifying an image from the database comprises one of:
matching the thermal insulation level of clothing worn by the user at the destination with a thermal insulation level of clothing worn by the user in the one or more images including the user;
matching the thermal insulation level of clothing worn by the user at the destination with the thermal insulation level of clothing worn by the crowd in the one or more images including the crowd; or
matching the thermal insulation level of clothing worn by the user at the destination with a thermal insulation level of clothing in an image from a vendor.

14. The device of claim 13, wherein the one or more processors further execute the instructions to:
display the image from the vendor to the user, wherein the image from the vendor has a link to a website of the vendor, the website available to sell the clothing in the image from the vendor to the user.

15. The device of claim 13, wherein recommending a style of clothing to the user includes one of displaying the matched clothing worn by the user in the one or more images including the user, or displaying the matched clothing in the image from a vendor when the clothing in the image from a vendor was previously viewed at a website of the vendor.

16. A non-transitory computer-readable medium storing computer instructions for determining thermal insulation levels for clothing at a computer or mobile device, that when the computer instructions are executed by one or more processors, cause the one or more processors to perform the steps of:

determining a thermal sensitivity bias for a user by averaging multiple comparisons of the thermal insulation level of clothing worn by the user to thermal insulation levels of clothing worn by a crowd of individuals in the one or more images at a same time, location, and environment;

collecting environment data based on at least one of time and location of a destination from a database;

predicting the thermal insulation level of clothing worn by the crowd for the destination based on the destination and the collected environment data;

generating the thermal insulation level of clothing worn by the user at the destination comprised of the thermal insulation level of the clothing worn by the crowd for the destination adjusted by the thermal sensitivity bias for the user; and identifying an image from the database having clothing with a thermal insulation level comparable to the thermal insulation level of clothing worn by the user at the destination.

17. The non-transitory computer-readable medium of claim 16, wherein:

analyzing the thermal insulation level of clothing worn by the crowd includes inputting the one or more images including the crowd into a trained second model, analyzing the thermal insulation level of clothing worn by the user includes inputting the one or more images including the user into a trained first model, and predicting the thermal insulation level of clothing worn by the crowd at the destination includes inputting the destination and collected environment data into the trained second model.

18. The non-transitory computer-readable medium of claim 16, wherein identifying an image from the database comprises one of:

matching the thermal insulation level of clothing worn by the user at the destination with the thermal insulation level of clothing worn by the user in the one or more images including the user;

matching the thermal insulation level of clothing worn by the user at the destination with a thermal insulation level of clothing worn by the crowd in the one or more images including the crowd; or matching the thermal insulation level of clothing worn by the user at the destination with a thermal insulation level of clothing in an image from a vendor.

19. The non-transitory computer-readable medium of claim 18, wherein the one or more processors further perform the steps of:

displaying the image from the vendor to the user, wherein the image from the vendor has a link to a website of the vendor, the website available to sell the clothing in the image from the vendor to the user.

\* \* \* \* \*

UNITED STATES PATENT AND TRADEMARK OFFICE
CERTIFICATE OF CORRECTION

PATENT NO. : 10,592,960 B2
APPLICATION NO. : 15/847747
DATED : March 17, 2020
INVENTOR(S) : Y. Chu et al.

Page 1 of 1

It is certified that error appears in the above-identified patent and that said Letters Patent is hereby corrected as shown below:

In the Claims

Column 28, Line 25 (Claim 12, Line 2), please change "determine" to --determining--.

Signed and Sealed this
Twenty-eighth Day of July, 2020

Andrei Iancu
*Director of the United States Patent and Trademark Office*